(12) United States Patent
Tang

(10) Patent No.: US 10,358,196 B2
(45) Date of Patent: Jul. 23, 2019

(54) UNMANNED AERIAL VEHICLE SYSTEM AND METHODS FOR USE

(71) Applicant: Rujing Tang, Plano, TX (US)

(72) Inventor: Rujing Tang, Plano, TX (US)

(73) Assignee: Rujing Tang, Plano, TX (US)

( * ) Notice: Subject to any disclaimer, the term of this patent is extended or adjusted under 35 U.S.C. 154(b) by 0 days.

(21) Appl. No.: 15/914,162

(22) Filed: Mar. 7, 2018

(65) Prior Publication Data

US 2018/0194445 A1 Jul. 12, 2018

Related U.S. Application Data

(63) Continuation of application No. 15/158,518, filed on May 18, 2016, now Pat. No. 9,944,366.

(51) Int. Cl.
| | | |
|---|---|---|
| *B63C 9/01* | (2006.01) | |
| *B64C 39/02* | (2006.01) | |
| *G16H 40/67* | (2018.01) | |
| *B63C 9/00* | (2006.01) | |

(52) U.S. Cl.
CPC .............. *B63C 9/01* (2013.01); *B64C 39/024* (2013.01); *G16H 40/67* (2018.01); *B63C 2009/0023* (2013.01); *B64C 2201/027* (2013.01); *B64C 2201/042* (2013.01); *B64C 2201/12* (2013.01); *B64C 2201/128* (2013.01); *B64C 2201/205* (2013.01)

(58) Field of Classification Search
CPC .......... B63C 9/01; B64C 39/024; G16H 40/67
See application file for complete search history.

(56) References Cited

U.S. PATENT DOCUMENTS

| | | | |
|---|---|---|---|
| 7,264,204 B1 * | 9/2007 | Portmann | B63B 35/50 244/110 C |
| 9,561,852 B1 * | 2/2017 | Beaman | B64D 1/00 |
| 9,817,396 B1 * | 11/2017 | Takayama | G05D 1/0038 |
| 2010/0026007 A1 * | 2/2010 | Bevirt | B64C 31/06 290/55 |

* cited by examiner

*Primary Examiner* — Stephen P Avila

(57) ABSTRACT

A drone equipped with a camera, a wireless communication module, an acoustic sensor, a GPS receiver, software and collapsible floatation device patrols above swimmers. The camera and acoustic sensor capture the video and audio of the swimmers. The information is either streamed to a command center or processed by the onboard software. With audio and video analysis capabilities, software is used to detect a swimmer in distress (SID). Alternatively the information is streamed to lifeguard or volunteers all over the world to spot SID. Another detection method is to let swimmer wear a wearable emergency notification device, which sends wireless signals comprising GPS location data. A SID presses a button to indicate rescue request and the drones fly over by GPS signal guidance. Solar power is used as the optional power source of the drones, which would allow the to sustain operation for a prolonged period of time. Once a SID is identified, the drone or drones fly over the SID and drops the collapsible floatation device.

11 Claims, 23 Drawing Sheets

UNMANNED AERIAL VEHICLE SYSTEM AND METHODS FOR USE

BACKGROUND

1. Field of the Invention

The present invention relates generally to aircrafts, and more specifically, to an unmanned aerial vehicle (UAV) system and method of use.

2. Description of Related Art

Every year there are thousands of swimmers and water sports participants drowned in the world. Traditionally the swimming places are monitored by human lifeguards. They also serve as rescuers whenever a swimmer is in trouble. US National Life Saving Statistics shows that in 2014, there were 242 million attendances in beach, and there were 52,627 rescues and 4 million preventive actions. There were 60 drowning deaths. Worldwide these numbers are substantially higher.

A successful rescue by a human lifeguard relies on first of all, discovering the SID, secondly the time it takes for the lifeguard to get close to the SID, and lastly, it depends on the skill of the life guard. Each step is sequentially dependent, and each step is inferior to a drone lifeguard. For instance, discovering is typically by human's eyesight compared to drone's camera and multiple detection methods. Human lifeguard has to swim to the SID at an average speed of 2 MPH compared to drone's unfettered speed up to 30-50 MPH or even higher in the future. Human lifeguard is inefficient and sometimes even put the lifeguard in harm's way. In addition, the cost of human lifeguard is one of the main reasons why oftentimes there is no human lifeguard at all in many beaches and swimming pools.

Access to the swimmer in danger (SID) is carried out by swimming. Rescuing is by connecting the SID with a floatation device or with the lifeguard. These methods are inefficient and sometimes even put the lifeguard in harm's way. In addition, the difficulties to rescue someone far away from shore is even more difficult. Another hazard is the swimming pools in residential areas which claimed many young lives over the years. The various embodiments of the present invention intend to make lifeguarding automated from monitoring, searching to rescuing.

Man-overboard (MOB) has been a problem for ships ever since the beginning of water transportation. Today some of the challenges facing the navy ships and the crews are:

Detection—Detection is typically done by one or more dedicated human lookouts. It relies on human eyeballs, which is not always reliable and available, especially during night time. It also requires training and staffing for lookout posts.

Searching—Even if an MOB incident has been detected, sometimes it is hard to locate that MOB. Typically a binocular or a helicopter would be used to locate. 'All hands on deck' practice reduces the capability of the ship during searching.

Rescuing—A lifeline or a floatation device is thrown at the MOB if the MOB is close to the ship. If the MOB is farther away from the ship, the ship has to sail back and to be steered toward to the MOB, which is dangerous and may not be practical in battlefield. The MOB is hard to identify at sea. A helicopter sometime is dispatched to carry out the mission. But that diverts the helicopter's other objectives and also poses danger to the rescue crews on the helicopter.

Dangers facing the MOB—The time element is critical in saving the MOB. Drowning could happen within minutes if the MOB has no lifejacket. Hypothermia could kick in 20 minutes after staying in seawater.

Drills—MOB drilling is a routine drill, which requires all hands on deck. This is a huge cost and burden.

Existing projectors could project images onto a surface for human viewers to see. However, the object that the surface belongs to needs to be supported by a structure or needs to be rigid so its weight could be borne. It restricts the availability of such surface. In addition, a projector has to be supported by another structure as well, such as a desk top or a tripod. In some scenarios, people need to view videos or images without being restricted by the needs for a structure to support the weight of the screen or the projection source. There has been hardly possible for people to view a movie or an advertisement commercial anywhere they want. A fixed screen attached to a structure that ultimately is supported by the ground is needed. In emergency response, such as an earth quake, sometimes the only reliable broadcasting tool is radio, which lacks video capability.

Moving an object to a target location is a common task. But sometimes the target location is hard to reach by conventional means. Machinery could be too expensive or inconvenient for the circumstance.

One example is for a sea going vessel to send an object to another vessel or to a dock. At the same time the vessel must keep a safe distance from the another vessel to avoid collision. Traditionally sending an object over is done by throwing a rope or cable by a crewmember from the vessel. The practice has been like that for thousands of years, which has the problem of limited range and accuracy inherent with a human throw.

Another example is a person being stranded in a tall building in a fire breakout. Sometimes it is hard to reach that person by ladder or a helicopter. There are very few other rescuing options.

Drones are great in flying to a desired target location, but the payload of a commercial drone like a quadcopter is limited, typically not exceeding ten pounds, which is not sufficient for moving an object or a cable over that weight limit.

Picking up dog waste or trash in streets could be a headache. Many devices have been designed to that end, but they are not automated. Their usefulness is therefore limited. More generally, there are situations some objects need to be manipulated but the location of the object is hard to reach, such as putting nails on roofs.

Airborne object has the risk of falling down on ground which would damage property or injure people. This is especially problematic for an unmanned aerial vehicle (UAV). Some attempts were made to mitigate the risk. For instance, U.S. Pat. No. 6,471,160 presented a solution to put a parachute on the UAV when there is a falling risk. However, the design only partially addressed the problem of speed reduction but not the impact mitigation. Some moving parts such as the motor blades might be still a hazard to people even the parachute has been deployed. In addition, there is a certain height requirements for deploying the parachute.

Accordingly, although great strides have been made in the area of UAV technology, many improvements remain.

BRIEF SUMMARY OF THE INVENTION

An embodiment of the present invention uses drones, or flying robots equipped with floatation devices, camera, microphone, communication module, GPS receiver, and software to improve the current lifeguard practice.

One or more drones are flown over the beach or the water area where the swimmers are. Each drone is responsible for a relatively fixed area of the water surface to monitor. Each drone is either stationary in midair or in circular motion. The camera on a drone takes real time videos or pictures of the water surface below. The microphone picks up acoustic signals. In one embodiment, the swimmer has a portable emergency notification device. The notification device has a wireless transmitter for sending wireless signals to notify the UAV. In some embodiments, the wireless signals comprise GPS geo-coordinate information for identifying the location of the swimmer. The UAV's onboard communication sensor is able to pick up the signals containing GPS information from the notification device directly or indirectly. In some embodiments, the wireless signals work like a radio beacon for the UAV to home in. There are three primary methods to detect SID. They can be used in conjunction or separately in a variety of embodiments of the present invention, which will be elaborated later in the disclosure.

Once a SID is detected, the drone is directed by the command center, or automatically by its own software to fly over the SID and rescue. Typically a group of drones fly over a swath of water area to monitor and rescue swimmers. As a group, the drones swarm to the SID if there is one being detected, and each drone drops its floatation device to maximize the floatation device availability to the SID. The drones are connected to a command center wirelessly to share intelligence and coordinate movements. The height of the drones should be appropriate, from several feet to hundreds of feet, depending on the tasks and conditions. If the collapsible flotation device is to be released from a drone, then an appropriate height should be kept to allow the floatation device to land as close as possible to the SID.

The collapsible flotation device is made by lightweight and buoyant materials, such as Styrofoam. It is carried by a drone. The floatation device is collapsible by spring hinges in between multiple panels. There are other methods of making the floatation device collapsible, such as self air-pumping life ring similar to an airplane floatation jacket. The release of the floatation device is either triggered by the command center or by the drone itself, depending on different configurations. The self-release mechanism has a variety of choices.

In one embodiment, the floatation device is an automatic inflatable lifevest. The life vest inflates by itself upon touch water. There is a compressed gas canister connected to a sealed life vest. Similar products exist such as ONYX® A/M-24 Deluxe Automatic Manual Inflatable Life Jacket. The drone carries such life vest and releases upon arrival at the SID location.

In one embodiment, a pod or a housing is being fastened to the body of the UAV. A door is installed at the bottom of the pod, and could be opened to allow the content inside the pod to drop out. The life vest could be store inside the pod. When the UAV arrives at its destination, the door could be opened and the life vest is dropped from the pod. The door opening mechanism is controlled by a computer controlled servo. When the computer instructs the servo to move, the servo could latch or open the door.

In yet another embodiment, the pod design could be improved so that it could avoid the content inside being stuck during release. When the door is opened, a pushing rod inside the pod could push the content downward. The pushing rod is activated by a computer controlled servo.

In one embodiment, when the floatation device is released, a line is connected to the floatation device. In some circumstances, the floatation device may not be exactly dropped to the hands of the SID, the UAV could move in mid air and drag the line so that the floatation device could be moved to the hands of the SID. Then the line is severed. To control the tension of the line, one method is to put the end of the line on a reel, and the reel is fastened to the UAV and could be controlled to reel the line. This accurate delivery method using line and reel could also be used in other payload delivery.

In yet another embodiment, the UAV carries a device, which could be a robotic device, a mechanical device, or any other device. The device could be released once the UAV reaches its destination having a line connected between the UAV and the device. One end of the line is spooled onto a reel. The reel could be fastened to the UAV or the device itself. A computer controls the reel's reeling motion. Controlling the speed of the line being released from the reel equates to controlling the release speed of the device. Therefore the device need not be in free fall, which is safer and more accurate. Furthermore, the UAV could maneuver in mid air so that the line could drag the device to its desired destination with high accuracy. The line could be severed after the device is delivered to its destination.

The three primary methods of detecting a SID are: audio/video signal analysis, human monitoring, and wireless signal form a wearable device worn by a swimmer. There are other methods for detecting SID as well.

A drone captures real time video/audio feed of the swimmers. In one embodiment, the video and audio signals are transmitted wirelessly to the remote information processing center, or the command center. The software at the command center is capable of detecting SID by analyzing the videos or images, in conjunction with audio analysis. Most SID has distinct patterns of moving of his or her body parts. For instance, a SID may wave arms violently, and the head may appear submerged in the water. There may be audio signal like 'Help!' from the SID or people around him. The audio signal processing software first establishes human voice baseline in that particular swimming environment. It is typically the average frequency and decibel level over a period of time. Then the software tries to distinguish any deviation from that baseline. When a swimmer or someone else yelps "Help", the frequency and decibel level, as well the voice recognition are used to identify as a potential rescue signal. In addition, the location of the yelp is also detected in three ways. One is from drone group location triangulation.

Each drone from the swamp picks up different level and direction of voice source, and the software is able to deduce the approximate location of the sound source. Another way is to equip a drone with direction sensitive microphone to locate the source of the voice. The third way is to make the drone change positions swiftly to identify the source of the rescue request sound. The video signals are analyzed to detect a typical SID body movement. The frequencies of arm movements as well as the position of the arms of a SID are very different from those of other swimmers. Image processing software is able to detect the differences. The software tracks every swimmer's head position. The head of a SID tends to be moving up and down close to the water level. In addition, the body of a SID tends to be straight up in the water, which is different from a normal swimmer. There are other clues that the software can capture and analyze to determine a SID.

Human monitoring is the second method of detection of a SID. The audio/video feed is monitored by either on-duty lifeguards or other people who care. In one embodiment, the audio/video feed is live streamed through internet and accessible by ordinary citizens or volunteers around the world though a web page. Many volunteers are willing to spend their time for monitoring and saving swimmers as pro bono effort. Once a volunteer spots a likely SID, a notification is sent by him or her to the command center for rescuing attempt.

The third method is to use waterproof emergency notification device worn by the swimmers. If a swimmer feels in distress, he simply presses a button of the device. The device transmits rescue signal wirelessly either directly to the drones or to the command center, with GPS information of the swimmer.

The drones receive the rescue request directly or from the command center, along the GPS information. A drone is equipped with GPS receiver that guides it to fly over the specific geo-coordinates indicated by the rescue request signals.

The present invention includes a lifeguard drone system to detect, search, rescue and retrieve in a man-overboard incident. Our system is stationed on a ship and surveils the nearby water surface with infrared cameras. Once a man-overboard (MOB) situation is detected, the lifeguard drone flies out of a housing. It then homes in toward the man-overboard, and hovers directly above the MOB upon reaching the MOB location. A floatation device such as an inflatable tube is released from the drone's payload for the MOB to hold onto. Furthermore, by delivering a specially designed fishing line payload to the MOB, retrieving the MOB become as easy as reeling in a fish without requiring the ship to sail back or change course. The system is largely automated.

The system has considerable advantages compared to existing solutions: (1) Expeditious detection, search, rescue and retrieval of an MOB, cutting time by at least 75% (e.g. detection is done automatically in a couple of seconds; the drone flies 3,000 feet in a minute). Greatly improves the survival rate of the MOB. (2) Reduces personnel/training/drilling/costs by at least 50%. (3) Drastically reduces the danger for the MOB, rescue crews and the ship. (4) Autonomous or semi-autonomous, 24/7 availability. (5) 'Swiss army knife' type of payloads for easy swap in and out of the drone, which could carry and drop other rescue equipment: e.g. a thermal unit to fight hypothermia, a radio (optional) for immediate communication, a sea dye marker, a fishing line spool for retrieval and etc. (6) The drone sends live video stream back to the people on duty (optional). (7) The drone hovers above the drowning person to give a clear indication of the whereabouts of the target. (8) The drone carries a mega phone, which could talk directly to the MOB. (9) Identifies man-overboard by passive means to keep radio emission control (EMCON).

An embodiment of the invention comprises a UAV and a loudspeaker fastened the to body of the UAV. The loudspeaker is connected to a wireless communication module. Alternatively the loudspeaker could be playing sound from a memory medium that is connected to the loudspeaker. The wireless communication module or the memory medium is onboard the UAV. The loudspeaker plays the sound it receives wirelessly while the drone is airborne. The loudspeaker draws power from a batter that is being carried by the UAV.

One simplified method is to connect a cellular phone or a cellular phone module to the loudspeaker. By dialing that cellular phone's number anywhere, a user could connect to the cellular phone, whose sound output is sent to the loudspeaker to be amplified. It is useful in crowd control, emergency response, search and rescue missions, and other use cases.

Some loudspeaker has strong magnet which potentially could interfere with the UAV's navigation system. A magnetic shield sometime is applied between the loudspeaker and the UAV navigation system. There are many choices for accomplishing this shielding effect. For instance, a metal sheet or foil could be used to minimize the magnetic interference.

Further, a microphone might be also fastened to the body of the UAV for picking up sound signals from the environment. Noise cancellation technique could be employed to reduce the interference from the propellers of the UAV. The sound signal could be transmitted wirelessly via a wireless communication module onboard the UAV to a remote destination.

An embodiment of the disclosed invention uses drones, or flying robots, or unmanned aerial vehicle (UAV) carrying video projection equipment, audio equipment, communication module, and fly control module to project video images or a still image onto natural or man made surfaces for people to view. One or more drones are used to spread a screen in mid air so that video images or a still image could be projected thereon.

The drone that is able to project images, or "Projecting Drone" (or "PD") projects light, a still image or video images. The video or image content source comprises an onboard storage medium, or wireless signals. The control of the PD's position in 3-D space and flight parameters such as speed and bearing are either from PD's onboard software or wirelessly transmitted instructions. In some embodiments of the present invention, speaker is installed on the PD to accompany the video or images.

The video projecting functionality is accomplished in a number of ways. In some embodiments, a video projector is fastened to the body of a drone. In other embodiments, a drone integrates all or parts of the functionalities of a typical projector, comprising lens, light source and the necessary circuitry. In yet another embodiment, the drone is equipped with mirror or other reflective devices to reflect light sources from other places.

The images of the video are projected onto man made or natural surfaces such as building surfaces and ground.

In one embodiment, one or more other drones are used to spread a screen in mid-air, and in later description one such drones are referred as 'Screen Spreading Drone", or SSD. Drones are flown to desired position for the screen to be spread. Each drone is fastened to a portion of the screen, either directly or through connecting components such as tethers. The forces exerted by the drones make the screen spread. Because the drones are able to exert forces in different directions, the spread of the screen is made easier. The force may come from the movement of the drones' bodies, or from onboard components of the drones, such as reels reeling the tethers, and the rotating wings. The reel that reels the tethers connecting a drone and the screen is driven by either a motor or spring, and is onboard the drone. The reel is automatically adjusted for the tension it asserts on the tether to keep the screen from unwanted movement. The PD or video devices from other places project images onto the screen for people to view. The size of the screen varies, depending on factors such as the coverage area, the content, the angle of the screen with respect to the ground, the height, the brightness of the video and ambient brightness. The screen is the surface of an object, which takes a variety of geometry forms comprising flat, warped, spherical or any geometric form. In addition, the viewing area, which a viewer can see, could be in any shape, such as circular, rectangular or any other shape. The viewers could be situated anywhere, such as indoors or outdoors, on the ground, in the water or even in mid air themselves. In one embodiment, an enclosure pumped with air or other lightweight gases is tethered with the SSDs, and its surface is used as a screen for image display.

The SSDs and PD are coordinated for synchronized motions in midair. The screen could be turned, moved, or in other types of motions as a result of the motions of SSDs. Likewise the PD moves to project images from different angle, height, distance to a surface. The motions create sophisticated viewing effect on the surface. In some embodiments, the movements of the drones are from the flight command sent from a command center, while in some other embodiments, the movements are from the drones' onboard software. In some embodiments, the drones are equipped with GPS location devices that allow them to know the current position as well as future expected positions. In some other embodiments, the drones know their relative positions with each other as a group by wireless communication and algorithms.

The apparatus or a group of apparatuses is used for entrainment, advertisement, public broadcasting, and emergency broadcasting. The apparatus is suitable both for indoor and outdoor use. There is no specific requirement for ambient light, although generally lower ambient light works better for video images.

The apparatus can be deployed in minutes in places where there is no display or screen, or no voice broadcast system.

The apparatus is ideal for a group of viewers to view. The content of the video/audio could be, but certainly not limited to, entertainment, advertisement, broadcasting, or emergency announcement or instructions.

In large-scale disasters, or riot scenario, a group of such apparatuses could be sent in the sky for the people to view the video or images. It would be a powerful disaster relief tool as well as peacekeeping tool.

Some embodiments of the invention are suitable for advertising otherwise hard to deliver, such as outdoors environments where it is traditionally difficult to set up screen and projectors. It takes a lot less effort to present to people using some of the embodiments of the present invention.

Traffic control traditionally uses billboards. It suffers the mobility, cost, information density, and availability issues. Some of the embodiments of the invention are used in midair with detailed guidance instructions for the traffic.

One embodiment of the present invention has an inflatable airbags secured around the airborne object, for instance, a UAV. A sensor is able to detect imminent falling, and sends a control signal to deploy the air bag. The sensor could be any combination of an accelerometer, an altitude meter, or GPS receiver. In addition, the airbag could be activated by user instruction or software instruction. The air bag would be deployed in mid air before the object touches the ground. The air bag provides a cushion to the impact, thereby reduces the damage after crashing.

The Design of the air bag has many choices. The type of airbag that is typically seen in vehicles could be a choice. In some embodiments, the airbag is connected to compressed gas canisters. When the sensor tells the airbag to deploy, compressed air inside the canisters will fill a sealed airbag. Typically the filling only takes a couple of seconds before the object falls onto ground. The airbag could take many different shapes once deployed. Since the purpose is to minimize the damage after a crash, the deployed airbag need to cover as much parts of the UAV as possible. In some embodiments, the airbag resembles a ball that encloses the UAV inside. The airbags could be made into different geometric shapes, such as shapes, ring shaped, or any other shapes.

The airbag is fitted around the UAV before it is deployed. It could be folded and or affixed to the body of the UAV. The aerodynamic and the function of the UAV would be impacted minimally with folded airbags.

In special moving parts such as propellers and etc, airbags could be installed around them for safeguarding.

The sensor could be automatic or manual. An automatic sensor could use modules such as accelerometers to detect abnormal behavior of the UAV in mid air. Another choice is to detect the altitude of the UAV. If the UAV is descending under certain altitude, or the UAV is descending a distance under a given time period which indicates lost of control, then the sensor will start deploying the airbag.

Under manual activation mode, a human operator or software could initiate the deployment of the airbag. The command signal is received by the UAV wirelessly.

A drone or an unmanned arterial vehicle (UAV) is an aircraft without a human pilot aboard. Its flight is controlled either autonomously by onboard computers or by the remote control of a pilot on the ground or in another vehicle. An embodiment of the invention uses a drone to carry a gradually sturdier tether (GST) in moving an object to a designated place. A GST is a tether or multiple tethers connected to have the characteristics of getting sturdier along its length. Sometimes being sturdier means a segment is made with a heavier material or the same material but thicker than another segment. In many cases that also means the GST is getting heavier per foot along its length. One example of a GST is a tether starts with a long thin thread made of nylon as thin as a tooth pick, and is securely connected to a heavier and sturdier rope, whose another end is connected to an iron chain. The breaking strength of the portion closer to one end is at least twice of that of the portion to the other end of the tether. The weight per foot of one segment of the GST could be at least twice of that of another segment of the same GST, because weight per foot increases as breaking strength increases. In some embodiments, a GST is formed by connecting a plurality of segments, each segment is made of different materials such as thread, rope, chord, cord, chain, tether and the like, usually in an increasing order of sturdiness along the length. In some embodiments, a GST is made with the same material but different construction along the length. For example, a lower breaking strength end portion is made of two strands of rope, and the sturdier end portion is made of 16 strands of the same rope material, each strand being the substantially the same as the individual strand of the lower breaking strength end portion. Between them there are other segments of the same rope material with varying number of strands, such as 4, 8 and 10 strands of the same strand of rope.

The sturdier end portion of the GST is tied to an object useful for the target location. A drone such as a quadcopter drone is quite agile to fly to a target location but typically cannot carry heavy weight with it. In most drones commercially available today, the maximum payload weight is generally less than 3 times of the weight of the drone. A typical commercial drone has a range of weight for different applications. With the help of a GST, the drone can fly with the less sturdy and usually light weight portion of the tether to the designated location leaving the weight of the sturdier and usually heavier portion of the tether on the ground or supported by a structure. In this way, the drone does not have to bear the whole weight of the GST while in midair, only the light portion of it. Once the drone flies to the desired target location, a human or a machine gets hold of the GST, the human or the machinery may pull the GST to move the sturdier and usually heavier portion of the GST closer to the location, along goes the object. Frequently the sturdier end of the GST is connected to a heavy object, which is useful for that location.

The tether is generally longer than 5 feet. It could be made considerably longer than 5 feet for different applications. In one embodiment, a drone is tied to a GST's segment with lower breaking strength, i.e. less sturdy portion, which is a sufficiently long thin thread made of nylon or the like. The rest of the GST rests on the deck of a sea going vessel. The drone flies with the thin end of the GST to the mooring post of a dork. A dockworker on the dock gets hold of the drone and picks up the thin thread, and start gradually pulling the rest of the GST. The heavier and sturdier section of the GST is gradually led by the lighter and less sturdy segment of the GST to the mooring post. Eventually the crewmember is able to fasten the mooring chain to the mooring post. In this case the desired object is the heavy mooring chain itself.

In construction, frequently there is a need to move an object to or from different places. It is usually done by a crane especially when the two places have an elevation difference. With some embodiments of the invention, it can be accomplished without a crane. For instance, a bucket needs to be lifted from the ground to the $10^{th}$ floor during the construction of a building. A GST is made with a sufficiently long thread made of nylon or the like, tied to one end of an iron chain whose another end is tied to the bucket. A drone tied to the less sturdy end portion of the GST, that is the nylon thread or the like, flies to the target location on the $10^{th}$ floor. A worker on the $10^{th}$ floor uses a combination of reels and pulleys to move the rest of the GST and thus hoists the bucket to the $10^{th}$ floor.

Another application is for transferring materials or making connections between two sea going vessels. The drone could be flown from the first vessel and landed on the second. The lower breaking strength and usually lighter end portion of a GST is attached to the drone so the second vessel could get hold it after the drone is landed. The crew on the second vessel pulls the segment with lower breaking strength. Gradually the sturdier portion of the GST could be secured by the second vessel to make a strong link between the two vessels. A pulley system could be established for transferring materials, or a tugging cable could be fastened for tugging purpose. A refueling line could also be sent from the first vessel to the second vessel this way.

Yet another application is in rescuing people from buildings, especially high rise buildings. When a fire breaks out in a tall building, sometimes people found themselves stranded and could not get out. Helicopters have very limited access in many situations. Ladders of firefighters also present challenges in many circumstances. An embodiment of the present invention could be used to carry out rescue missions. Suppose a person is stranded by a window side on the 20th floor of a high-rise building, which is beyond most firefighter's ladder's reach. The drone carrying the end portion of a GST, which has lower breaking strength, could easily found its way to the open window for the person stranded inside the building to get hold of. The other end of the GST is tied to means for escaping, for example, a zip line, a chute slide, a link to a helicopter in midair and not directly above the building, or some other rescuing equipment. The person could pull the GST until the means for escaping reaches the window. Then the person could start escaping with some help from the ground. It took a drone a few minutes to fly to such height and is considerably faster than other means.

A helicopter could utilize one embodiment of the invention. The helicopter could release the apparatus from mid air. The drone has the less sturdy portion of a GST tied to its body, and the bulk of the rest of the GST stays inside the helicopter. After being dropped from the helicopter and descended to an appropriate height, the drone flies to a target location that is not directly under the helicopter. A person or a machine at the target location could get hold of the drone and the GST, and starts pulling the rest of the GST. Once the sturdier portion has been pulled to the target location, materials or personnel at the target location could be transferred to and from the helicopter. The advantage is that the helicopter does not have to be directly above the target location, which would greatly limit the use of a helicopter. The helicopter could release the drone from anywhere as long as the length of the GST allows.

The advantages of using the various embodiments of the invention would be helpful in rescuing or in military applications.

In some scenarios, the drone's target location is another aircraft, or an object attached to an aircraft in midair. The drone flies to the proximity of the object or the aircraft. The GST tied to the drone is secured by the target location, from which point the rest of the GST would be pulled so that a sturdier link could be established. This could be used in material or personnel transfer. Specifically for midair refueling, a drone could be used in this fashion so that a refueling hose could be connected between a fuel tank aircraft with an aircraft in midair, after the sturdy link is established. A helicopter refueling could be accomplished by establishing a sea based or ground based refueling station while the helicopter remains in midair, not directly above the refueling station.

In accordance with the invention, frequently self-release mechanism is used for the drone to connect with the tether. Upon remote or onboard software instructions, the drone's is able to release the tether automatically. This enables the drone to fly freely after the mission is accomplished, or when the continuation of the connection might endanger the drone or other equipment. The self-release mechanism is accomplished by using a micro controller on board the drone that controls a linear actuator or other types of actuator to effectuate a movement of a rod or a curve shaped member. By virtue of the movements of the rod or the curve shapes member, the tether can be released automatically. Other types of auto release mechanism is also available.

A drone connected with a tether could be analogous to a needle and a thread, which could weave a variety of structures made of the tether by moving the drone, as long as the drone is able to support the weight of the tether in midair. In this sense, the tether does not have to be a GST. Further the drone could move around an object multiple times and make the tether go around the object multiple times, therefore fastens the tether to the object. Moreover, a drone is able to make movement to form a knot using the tether. A drone could make movements based on computer control, which enables a drone to make patterned or complicated movements in accordance to computer instructions. This would make the tether form patterns or intricate structures in space.

In addition, in some embodiments, a plurality of drones are connected through tethers. If the drones and the tethers are in midair, as long as the drones are collectively able to life the tethers, the tethers do not necessarily have to be GST. For instance, two drones might be connected with a tether and be flown in a concerted manner. One application with this configuration is to use the tether as a blocking means to deny enemy aircraft. The tether could be made with material having appropriate characteristics including strength, for instance with material having tensile strength over 100 MPa. If an enemy jet or rotary wing aircraft comes into contact with the tether, the tethers could entangle the rotary wings or damage the jet engines of the enemy aircraft. A different configuration is also possible, which is connecting an air balloon and a drone with a tether to carry out air space blocking mission. Generally the tether would be a threat if it were moved to the proximity of an enemy aircraft, like within 100 feet of distance.

In winter ice and snow tend to accumulate on the overhead power or communication cables. The weight of the ice or snow sometimes could break the cable. A drone or multiple drones could be used to clear out the ice or snow accumulations. One method is to connect two drones with a tether, the tether touches the cable but at an angle with the cable. The two drones move the tether in one direction along the length of the cable. The movement of the tether against the accumulation clears it out.

The tether connected to a drone in many cases could also have power recharging capability. At least a portion of the tether that is connected to the drone is a conductive wire or wires, or the portion of the tether is bundled with a conductive wire. A recharging device is attached to the end of the wire. When the recharging device comes into contact to an appropriate energy source, the drone's onboard rechargeable battery could be recharged. This would give the drone more staying power in midair. The recharging could take place by induction or by contact. Further the tether could be retractable. The drone extends the tether to make contact to the recharging power source, or to be close to a recharging power source in induction recharging scenario. The recharging power source could be based on ground or in midair supported by an aircraft or even another drone. After the recharging is completed, the tether could be retracted by the drone.

Object manipulation mechanisms could be coupled to a drone, with or without a tether in between them. The object manipulation capability combined with the ability of a drone's reach could make this type of embodiments very versatile.

Further, In some embodiments, a drone is typically equipped with camera and optionally a microphone, a GPS receiver, and other types of sensors that can feed information about the environment to the drone or remotely to a human or a server. Software applications are used to analyze the images and the information to make decisions about the next action of the apparatus. The instructions are sent to the drone and the devices coupled to it to be carried out by the drone and the devices. For instance, a gripping mechanism could perform a variety of motions like a human hand, based on this control-feedback method.

There are numerous other usage scenarios for a variety of embodiments of the present invention.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
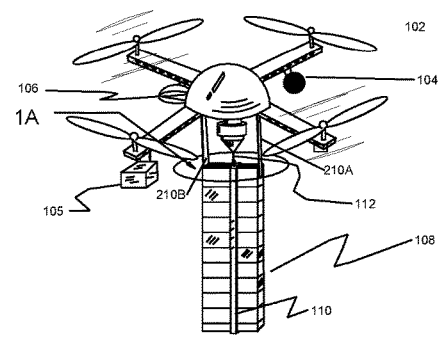
FIG. 1 depicts the detection and rescuing mission carried out by the drone with floatation device.
Figure 1:
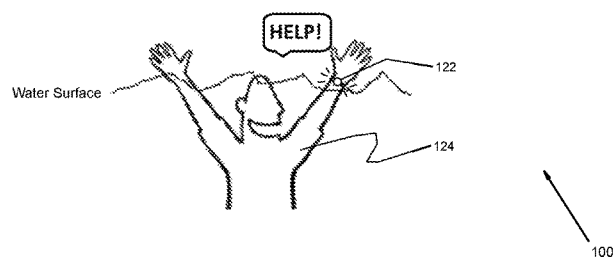

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
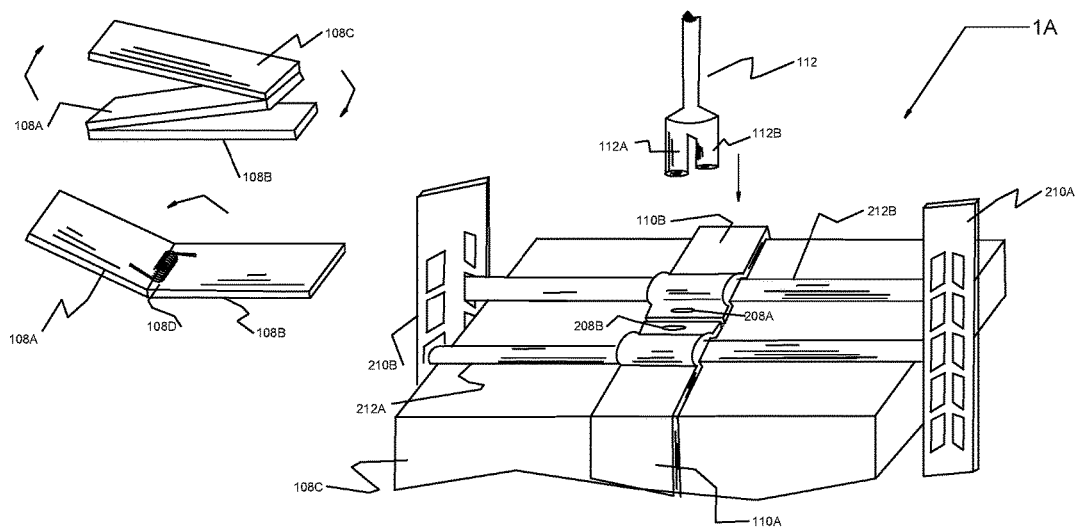
FIG. 2 depicts the details of floatation device and the collapsing and releasing mechanisms.

FIG. 1 depicts the detection and rescuing mission carried out by the drone with floatation device. The detection and rescue missions are illustrated in 100. The drone with the floatation device is illustrated in 102. The drone should be able to carry some minimum weight such as 0.5 kilograms. A microphone and/or loudspeaker communication device 104 and a video camera 106 are mounted in the drone to pick up audio and video input from the water below. A GPS receiver 105 receives geo coordinates. The collapsible floatation device is depicted in 108. A strip or case 110 wraps around the floatation device to prevent it from popping open. One end of pin 112 is fastened to the bottom of the drone and the other end is inserted in the holes of the strip 110. Identifiers 210A and 210B are the two supporting structures extending from the bottom of the drone. More details of the view of the plane 1A are shown in FIG. 2. A swimmer in distress (SID) is shown in 124. He wears a wearable notification device 122. He also yells "HELP!" as a SID would do. The audio and the video signals have been transmitted to a command center. The wearable device 122 also gives notification to the command center or the drone, with GPS location information. The drone flies over the SID 124 and is ready to drop the floatation device 108.

FIG. 2 depicts the details of the floatation device and the collapsing and releasing mechanisms. The floatation device 108 is collapsible into multiple adjoining panels such as 108A, 108B, and 108C. A spring hinge 108D is attached to the short sides of two panels 108A and 108B. If there is no outside force, the spring hinge 108D causes the two panels to lay flat side by side, as indicated by the arrow above the two panels. On the other hand, an outside force makes the two panels fold along their adjoining short sides. In similar fashion, another panel 108C is attached to the panel 108A, but along the other short side and on the other surface by a spring hinge. Multiple panels are thus collapsed if a force is applied perpendicular to the folding surfaces. When the force is removed, the spring hinges cause the panels to extend to its fullest, which make all the panels to be flat and joined by the spring hinges 1A indicates the same plane shown in FIG. 1. The force here is the case or strip 110 wrapping around the collapsed panels. 110A and 110B are the two ends of the strip 110. 110 is a strip made of rigid plastics with an open ends. There is a small hole close to each end, as shown in 208A and 208B, for the two prongs 112A and 112B of the pin 112 to insert and fasten. 210A and 210B are the two supporting structures extending from the bottom of the drone. Two cylindrical shafts 212A and 212B are fixed on the drone supporting structures 210A and 201B. The shafts 212A and 212B go under the strip 110's two ends 110A and 110B, respectively, holding the weight of the collapsible floatation device 108. To fasten and create an auto release mechanism, a pin 112 is used. One end of the pin 112 is attached to the bottom of the drone, and on the other end are two pronged pins 112A and 112B. The pin 112 is able to move vertically by the drone to lock or release the floatation device. When the two prongs 112A and 112B are inserted into the small holes 208A and 208B of the strip ends 110A and 1106, the strip is locked in its place and so is the floatation device 108. However, when the pin 112 is moved upward and leaves the holes 208A and 2086, there is no force to hold down the two ends of the strip 110A and 1106.

The imbalance of forces on the two sides of shaft 212A would cause 110A to detach from the surface of 108 and break loose, which also is the case for 1106, and that leads to the detachment of the entire strip 110 from the floatation device 108. As soon as the constrict of the strip is removed, the collapsible floatation device 110 falls from the drone, and the spring hinges cause the panels to extend to their fullest state. The extension will continue on the water surface if it is not completed during the fall. In other embodiments, a release hook with a spring is used instead of the simple pin to lock the hole and press down the ends of the strip 110.

Figure 3:
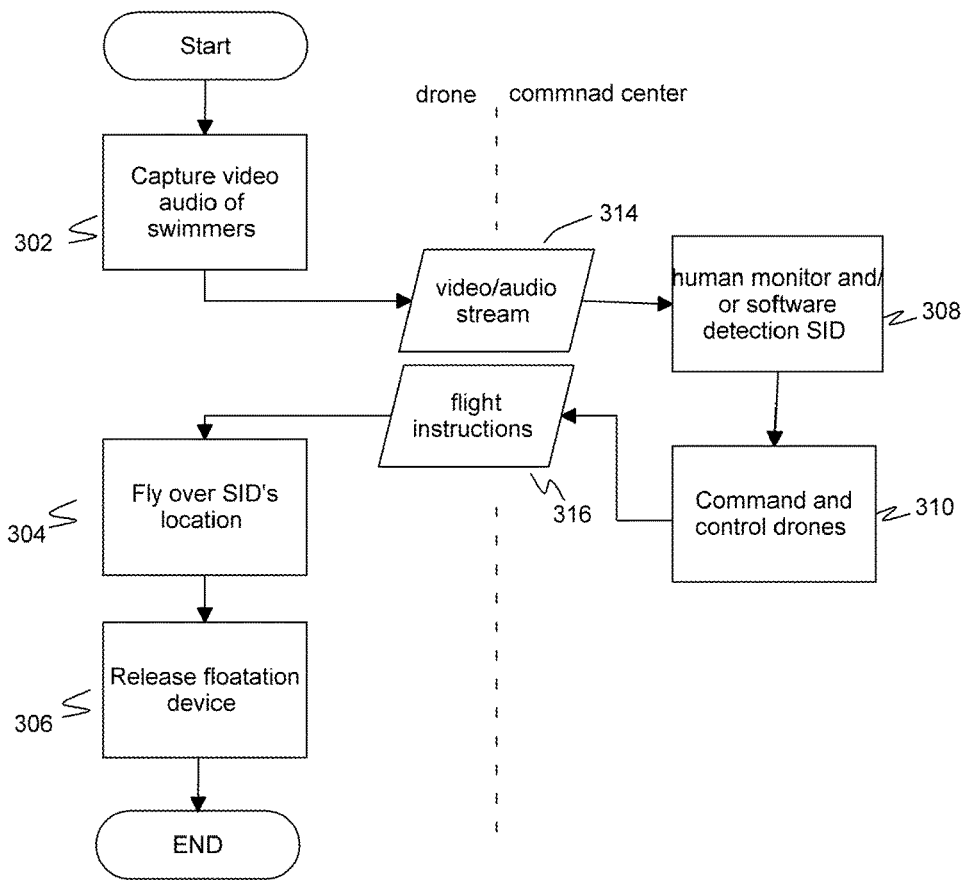
FIG. 3 depicts the process of the flowchart of monitoring and rescuing using audio and video signals.

FIG. 3 depicts the process of the flowchart of monitoring and rescuing using audio and video signals. On the left side of the dotted line is the flowchart occurring on the drone, while the right side of the dotted line represents the flowchart of what is occurring in the command center. In step 302, the drone's onboard camera 106 and device 104 in FIG. 1 capture audio and video information of the swimmers below. The live audio/video stream 314 is transmitted wirelessly to the command center for image and acoustic processing in step 308. Once a SID is found, the command center directs the drone's action by sending flight instruction 316 back to the drone. The drone flies over the SID's location according to the flight instruction 316. Once it reaches above the SID, it releases the flotation device in step 306. The image and acoustic processing step 308 could be accomplished by human beings, or by software. Human beings are excellent in spotting SID. One method is to live stream the video and audio to volunteers all over the world. There are many volunteers or human monitors who are willing to monitor the swimmers. If a SID is identified by them, they will notify the command center for further action, all through the Internet. Software is also suitable for the task of detecting a SID. A SID has some characteristic body movements and sound signature. For instance, the SID's body typically is vertical in the water, and the SID's hands are waving irregularly and rapidly. The head of a SID tends to be submerged. The yelp of "HELP!" could be captured in many cases. In other embodiments, part or all of the functionalities of the command center are handled by the drone.

Figure 4:
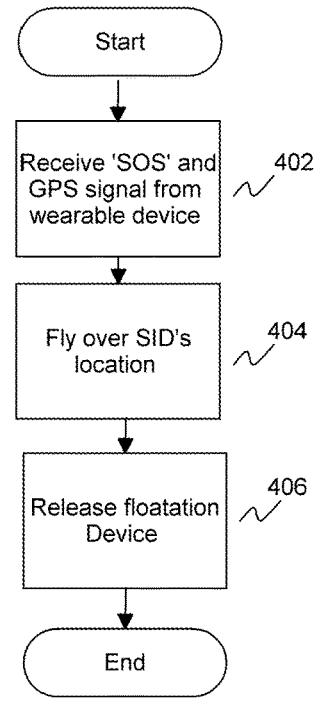
FIG. 4 depicts the flowchart of monitoring and rescuing when a swimmer wears emergency notification device.

FIG. 4 depicts the flowchart of monitoring and rescuing when a swimmer wears the portable emergency notification device. When a SID feels in distress, he would press a button on his wearable emergency notification device, which sends wireless signals either to a drone, or to a command center, or both. After the emergency signal is received in 402, the drone got the notification with the geo-coordinates of the SID's location. The drone is equipped with its own GPS receiver as shown in 105 in FIG. 1. It compares the relative bearing between its own location and the SID's location and deduces the route getting there in step 404. Once the drone is above the SID, it releases the floatation device for rescuing the SID in step 406.

Please note that sometimes the wireless signal from the wearable may be used as a radio beacon to guide the drone to home in on the portable notification device. GPS signals may not be an absolute necessarily in this case.

Figure 5:
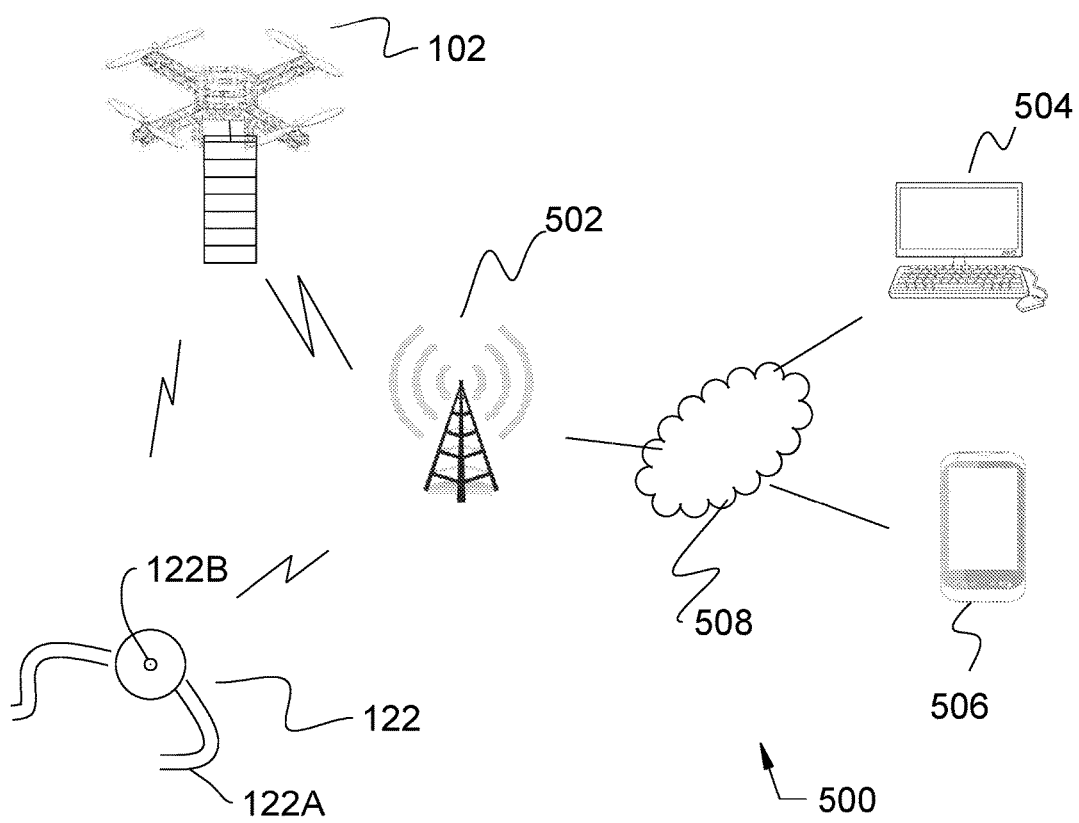
FIG. 5 depicts the system components of the primary embodiment of the present invention.

FIG. 5 depicts the system components of the primary embodiment of the present invention. System 500 depicts the overall architecture. It is to be noted that not every element needs to be included in all embodiments. For example, in some embodiments the drones are completely autonomous and do not require the command center, and are capable of carrying out the entire search and rescue mission. The drone 102 is also shown as 102 in FIG. 1. It communicates wirelessly with a base station 502, which in turn connects with the Internet 508. The command center 504 and a mobile device 506 are connected to the Internet and are able to communicate with each other. The wearable device 122 is also shown as 122 in FIG. 1. 122A is the strap to be attached to the swimmer's wrist, and the button 122B is used to send emergency signals. The emergency notification signal is sent to the base station 502 or is sent directly to the drone, depending on configurations. The emergency information includes geo-coordinate information so the drone can quickly locate the SID.

Figure 6A:
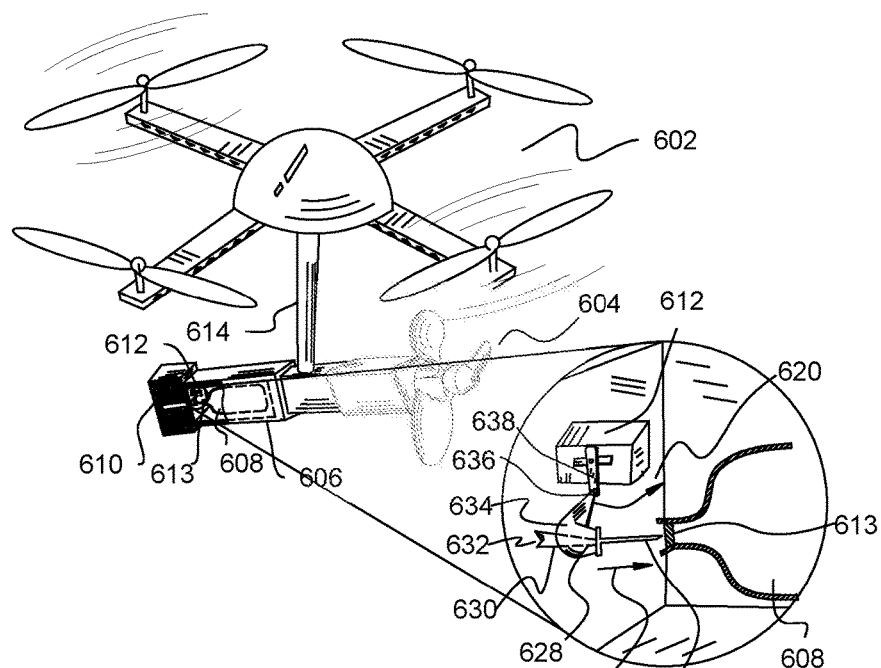
FIG. 6A depicts an embodiment that comprises a drone, a water propeller and an inflatable balloon, along with a compressed gas canister.

FIG. 6A depicts an embodiment that comprises a drone, a water propeller and an inflatable balloon, along with a compressed gas canister. 602 is a drone. 604 is a propeller to be used in water. The propeller 604 is connected to a connecting shaft 614, which is in turn connected to the drone 602. A compressed gas canister 608 is placed inside a housing 606, which is also connected to the connecting shaft 614. The compressed gas canister 608 contains pressurized gas, such as $CO_2$. The housing 606 that holds the compressed gas canister 608 is connected to an inflatable balloon 610. The opening of the inflatable balloon 610 leads to a hollow hole inside a plunger 628. On the one end of the plunger 634 is a pin 624 which is hollow for inducing gas to escape to a gas passage way 632. The pin 624 could be moved in direction 626 to puncture the seal 613 of the canister 608. That will allow the gas inside the canister 613 to escape into the inflatable balloon 610 via the hole 628, and the gas passage way 632 provided by a connector 630 which connects to the opening of the inflatable balloon 610.

A servo 612 is fastened to the inside wall of the housing 606. Its arm 638 moves in direction indicated by 620 to push the plunger 634 in the direction of 626. Identifier 636 is a pin axle connecting the arm 638 and the plunger 634. The servo's movement is under the control of the drone. During patrol mode, the inflatable balloon 610 is folded to save space and make the drone aerodynamic.

In some embodiments, the shaft is separable from the drone 602, which could enable to the floatation device 610 and the water propeller 604 to release from the drone.

Figure 6B:
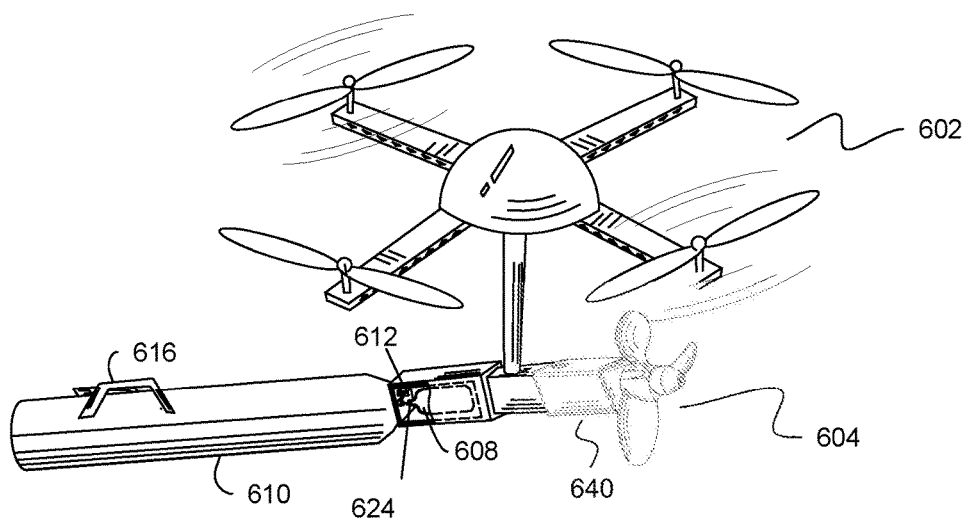
FIG. 6B depicts the same embodiment of FIG. 6A, wherein the inflatable balloon is inflated.

FIG. 6B depicts the same embodiment of FIG. 6A, wherein the inflatable balloon is inflated. If a SID is identified, the drone 602 flies directly over to the SID and descend on the water. The servo 612 under the control of the drone plunges the pin 624 into the canister 608 to release the compressed gas into the inflatable balloon 610. The balloon may have handles 616 for the SID to get hold onto. The water propeller 604 starts revving up once in water with battery housed inside 640. The SID holds onto the handle 616 to float on water. The propeller 604 provides the propulsion for the SID to swim back to safety. It is not too difficult for the SID to control the direction of the propulsion using the handles 616.

Figure 7:
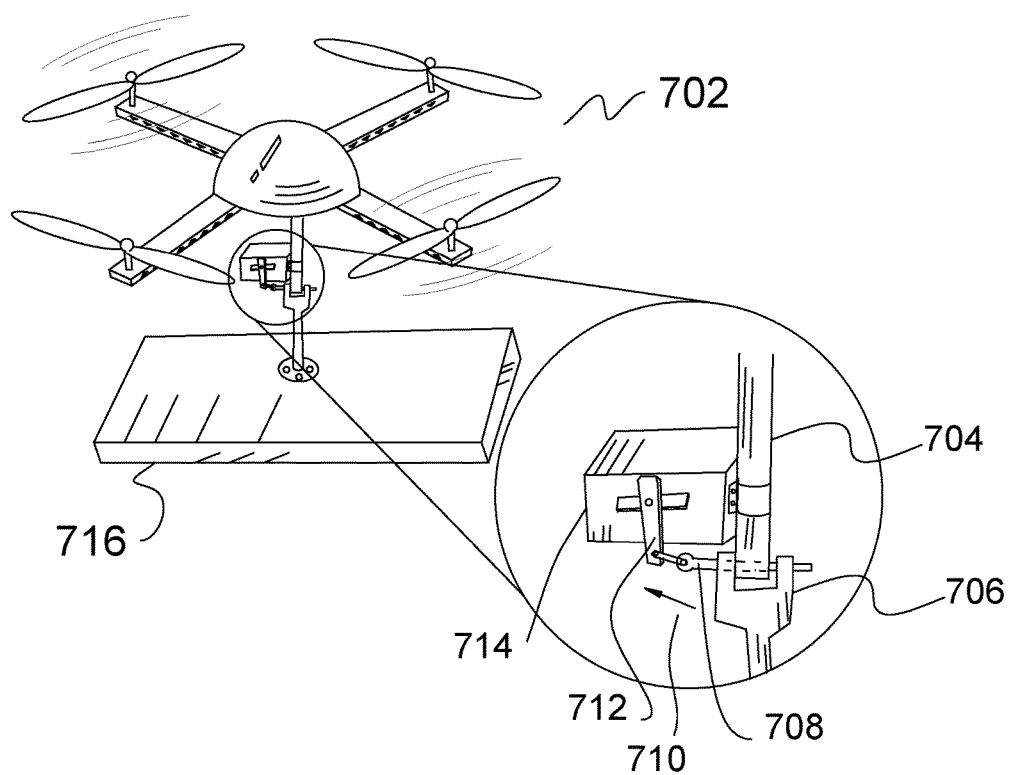
FIG. 7 depicts a release mechanism for the floatation device to drop from a drone.

FIG. 7 depicts a release mechanism for the floatation device to drop from a drone. Drone 702 is connected to a floatation device 716 through connecting rods 704 and 706. At the connecting end, rod 706 has a CU' shaped indent for the connecting rod 704 to fit in. There are holes on the two arms of the CU' shaped indent and the end portion of rod 704 to allow a pin to hold the rods together. A pin 708 goes through the holes inside both rods 704 and 706 to hold them in place. A servo 714 is fastened on rod 704, and its moving arm 712 causes the pin 708 to move in direction indicated by 710, which can disengage the rod 706 and 704 and release the rod 706 from the drone. The servo 714 is under the control of the drone.

Figure 8:
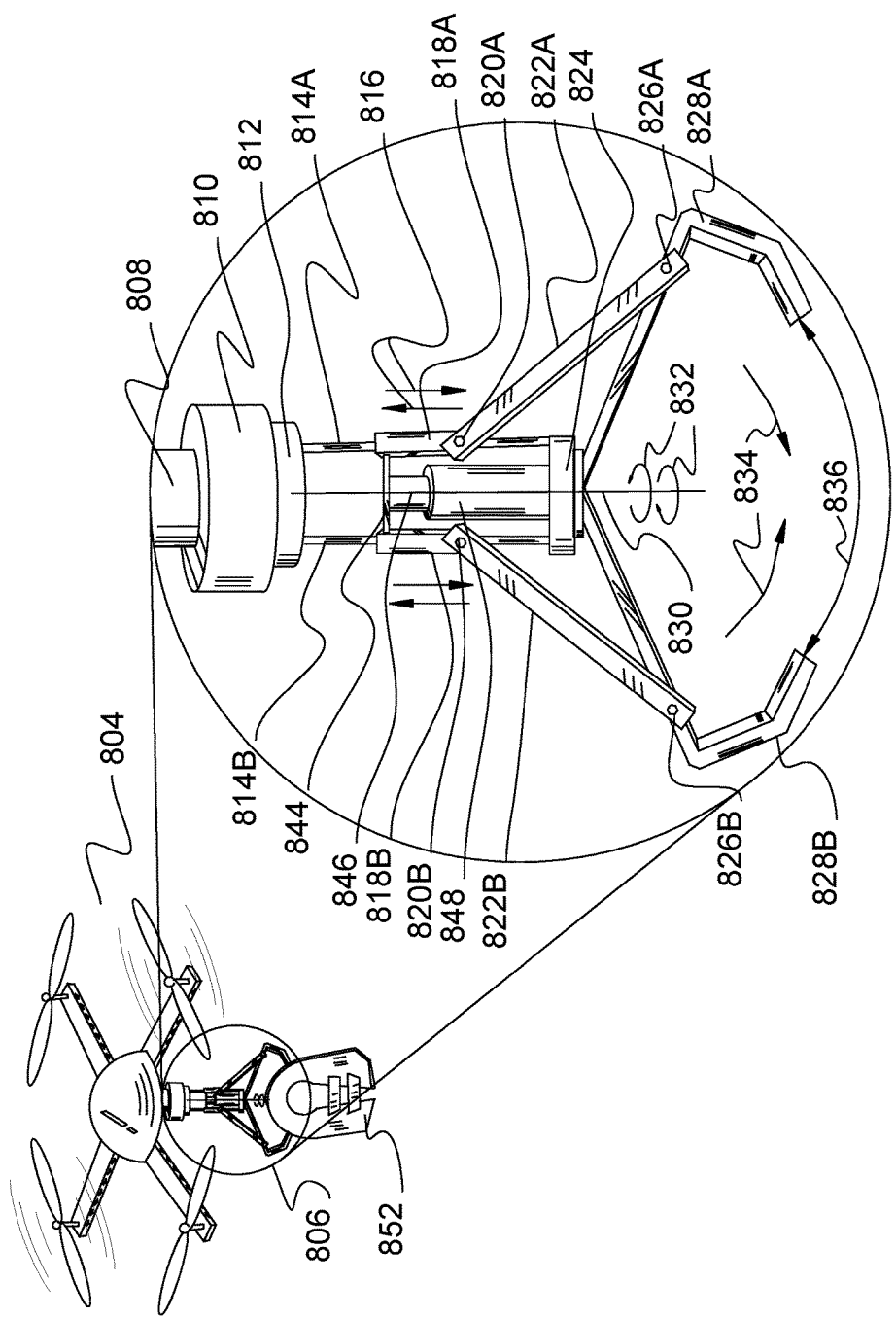
FIG. 8 depicts another release mechanism for the floatation device to drop from a drone using gripping fingers.

FIG. 8 depicts another release mechanism for the floatation device to drop from a drone using gripping fingers. The gripping mechanism 806 enables the drone 804 to get hold of a floatation device such as a life vest 852 and release it. FIG. 8 only shows one possible mounting position for the gripping mechanism. The life vest 852 is to be gripped or grabbed by the fingers 828A and 828B of the gripping mechanism 806, and could be released when the fingers 828A and 828B move away from each other.

A motor 810 is mounted on the mounting rod 808, the motor 810 enables the gripping arm and fingers to rotate around its central axis 830, in both directions as shown in 832. The ends of the guide rod 814A and 814B are fastened to the frame end members 812 and 824, which is directly coupled to the motor 810. When the motor 810 is in operation, its torque is transferred to the frame end member 812, which in turn make the rest of the gripping mechanism rotate around its central axis 830, in both directions as shown in 832. This rotating motion helps the gripping mechanism overcome possible resistance from a possible attachment between the object being gripped and some other object. For instance, when the drone is used to pick fruits like apples from a tree, after an apple is being gripped by the gripping mechanism 806, the rotating motion 832 around the central axis 830 makes it easy for the apple to break from its stem.

The frame on which the actuator housing 848 is installed comprises a frame end member 812, another frame end member 824, and two guide rail 814A and 814B being parallel to each other. The guide rails 814A and 814B are fastened to the frame end member 812 and 824, and are perpendicular to the two frame end members 812 and 824. The housing of the linear actuator 848 is fastened to the frame end member 824, while the thrust rod 846 of the actuator is able to move along the central axis 830. The top plate 844 is joined to the end of the thrust rod 846. The top plate 844 is further fastened to two moving tubes 818A and 818B respectively. The two moving tubes 818A and 818B are fitted to the guide rod 814A and 814B, respectively, which can move in both directions as shown in 816 along the guide rods 814A and 814B. The ends of the right gripping arm 822A and the left gripping arm 822B are connected with the moving tubes 818A and 818B through rotatable couplings 820A and 820B, respectively. The other ends of the right gripping arm 822A and the left gripping arm 822B are connected to the right gripping finger 828A and 828B through rotatable coupling 826 A and 826B respectively. The movement of the top plate 844 away from the actuator housing 848 makes the moving tubes 818A and 8186 move upward, away from the actuator housing 848, along the guide rods 814A and 814B respectively. That motion in turn causes the up ends of the gripping arms 822A and 822B to move upward because of the coupling 820A and 820B, respectively; and causes the lower ends of the gripping arms 822A and 822B to move inward toward the central axis 830, because of the couplings 826A and 826B, respectively. As a result of the inward movement of the gripping arms 822A and 822B, the gripping fingers 828A and 828B moves toward the central axis 830, as shown in direction 834. When the top plate 844 moves down and toward the actuator housing 848, the motions of the moving parts are reversed, resulting in the opening of the gripping fingers 828A and 828B, as shown in the direction of 836. The two directions 834 and 836 correspond to the gripping motion and releasing motion of the gripping mechanism respectively. When the gripping fingers 828A and 828B open in the direction 836, the floatation device 852 is released from the drone.

Figure 9:
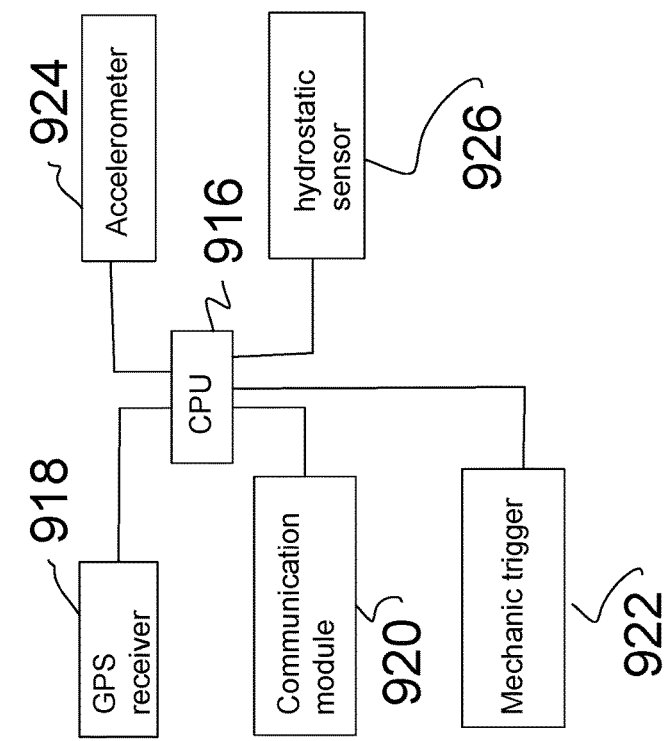
FIG. 9 depicts the structure of the wearable emergency notification device.
Figure 9:
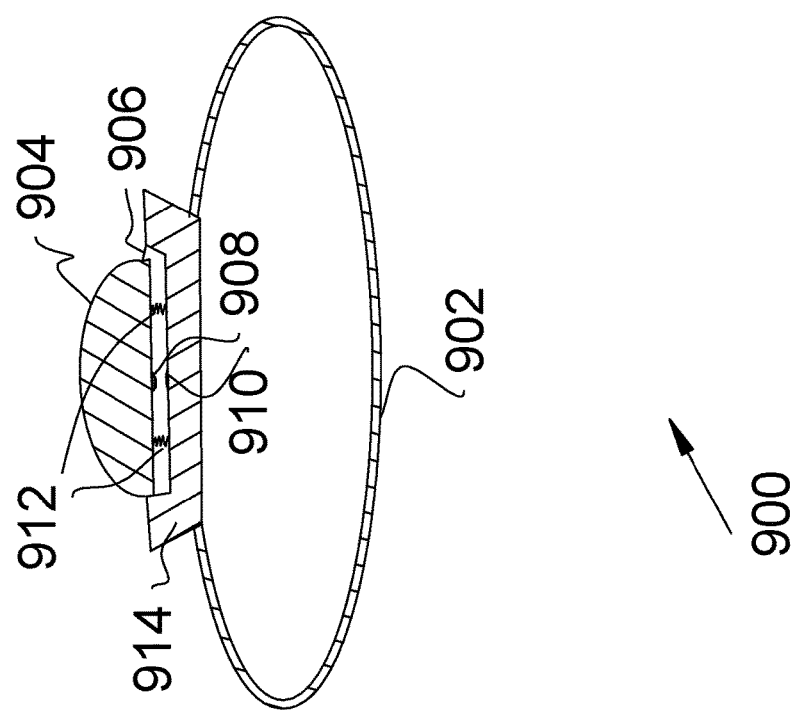

FIG. 9 depicts the structure of the wearable emergency notification device 900 is the sectional view of the emergency device also shown as 122 in FIG. 1 and FIG. 5. 902 is the band to be worn around wrist or other body parts. 904 is the button that sits on top of two springs 912. Water proof rubber seal 906 prevents water invasion into the device. 908 and 910 are conductors connected to the button 912 and the base 914 respectively. Once the button 904 is depressed, the conductors 908 and 910 come into contact with each other and close a circuit to trigger emergency notification. Inside the casing of the base 914 is the hardware of the device that is depicted on the right side of the FIG. 9. The mechanic trigger 922 refers to the trigger caused by the contact of conductors 908 and 910. The CPU 916 detects the trigger and starts sending out 'SOS' signal and the geo-location information collected from the GPS receiver 918 via the communication module 920.

In some embodiments, an accelerometer 924 and a hydrostatic sensor 926 are added to detect abnormal arm movements. The hydrostatic sensor 926 is used to tell if the device is above or submerged under water; and if submerged, the device's submerge depth. A drowning person's arms tend to move erratic relative to water surface. For instance, statistics and experiments may suggest that a drowning person's arms would move above water surface in vehement but short burst of back-and-forth movement.

In addition, sensors that measure the wearer's biometric information could be used. Information such as the user's heart rate, blood oxygen level, breathing pattern, and other vital signs could be used for determining whether the user is under stress. Using these types of patterns and user's physical vital sign information, the CPU 916 is able to determine whether or not the wearer is in drowning danger. If the CPU 916 determines that the wearer is in drowning danger, a 'SOS' notification and GPS information would be sent via the communication module 920. It is possible to add other detection sensors to the notification device, such as camera, microphone, /loudspeaker communication device biometric or vital sign sensors and so forth to further enhance the detection accuracy. In conjunction with the present disclosure, those skilled in the art will be able to design and incorporate any one of the variety of mechanisms suitable for accomplishing the above described functionalities.

It is to be understood that the disclosure teaches just one example of the illustrative embodiment and that many variations of the invention can easily be devised by those skilled in the art after reading this disclosure and that the scope of then present invention is to be determined by the following claims.

Figure 10:
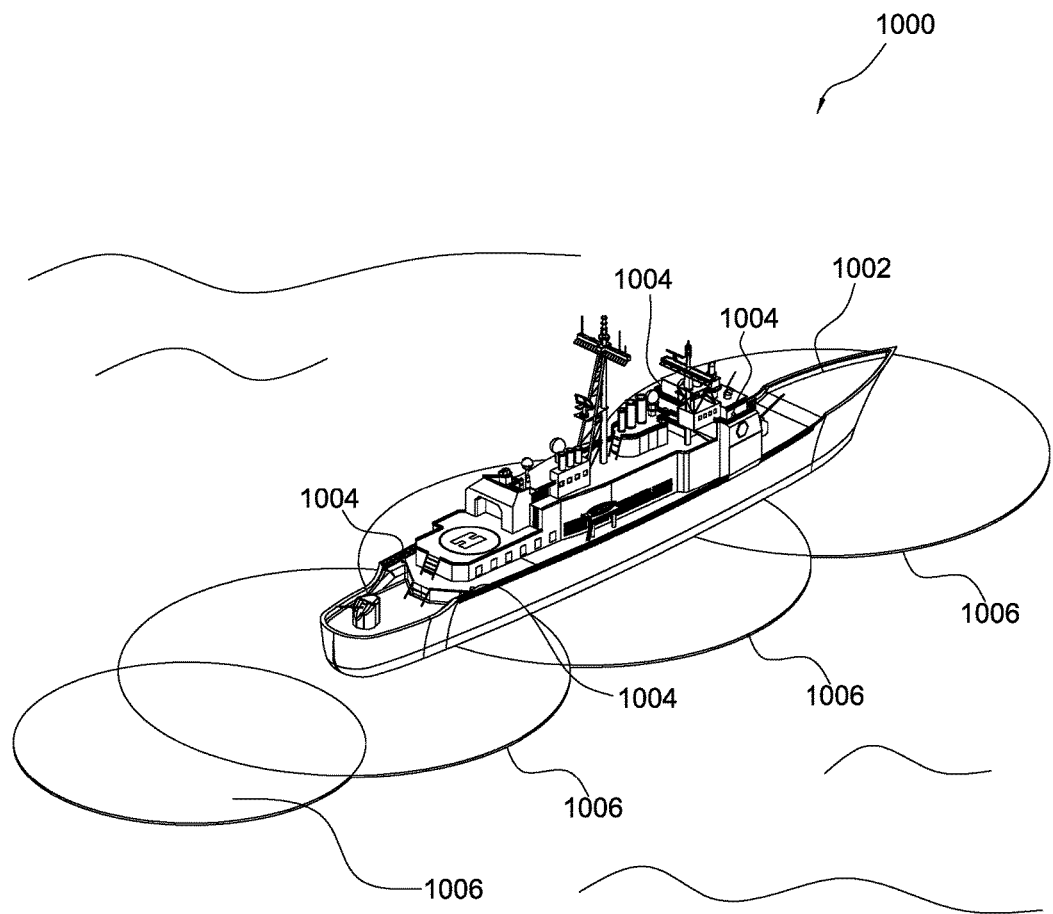
FIGS. 10-14 are oblique views of the system of FIG. 1 during use.
Figure 11:
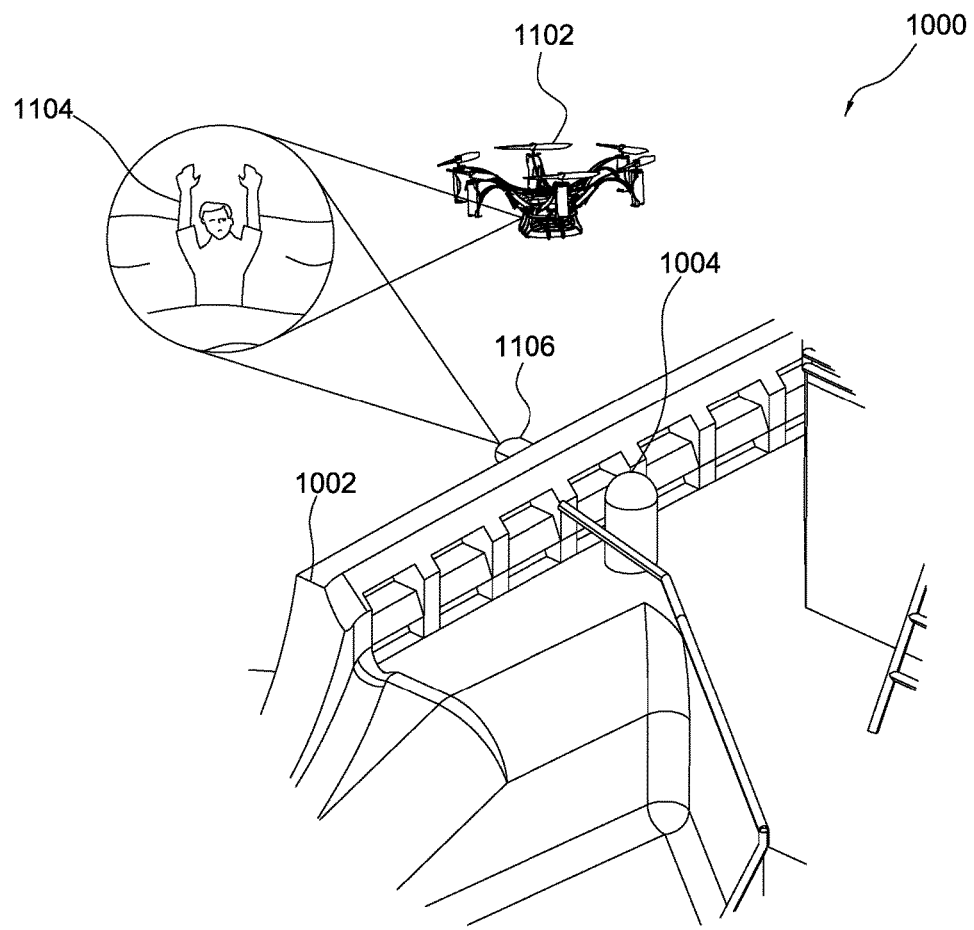
Figure 12:
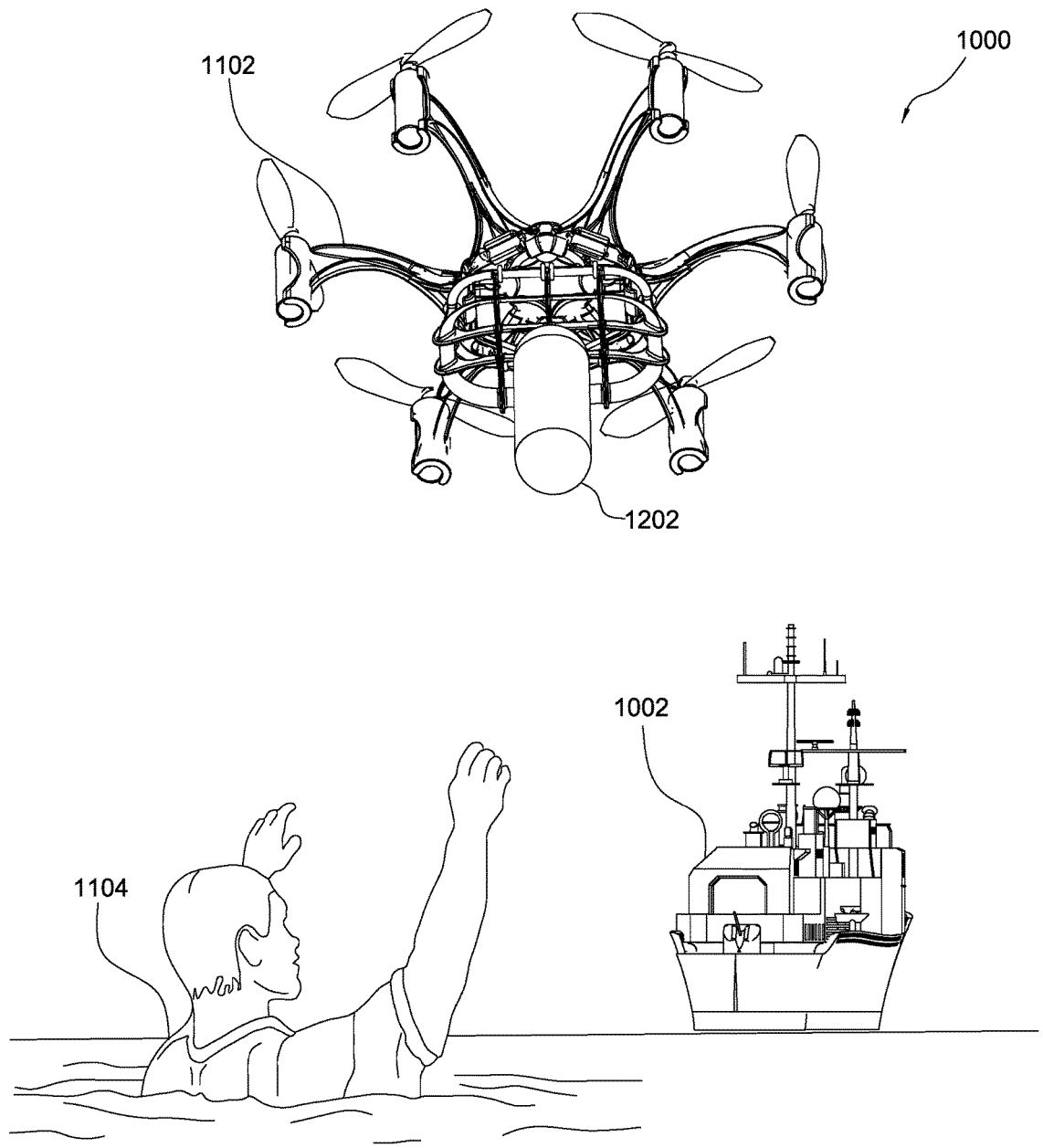
Figure 13:
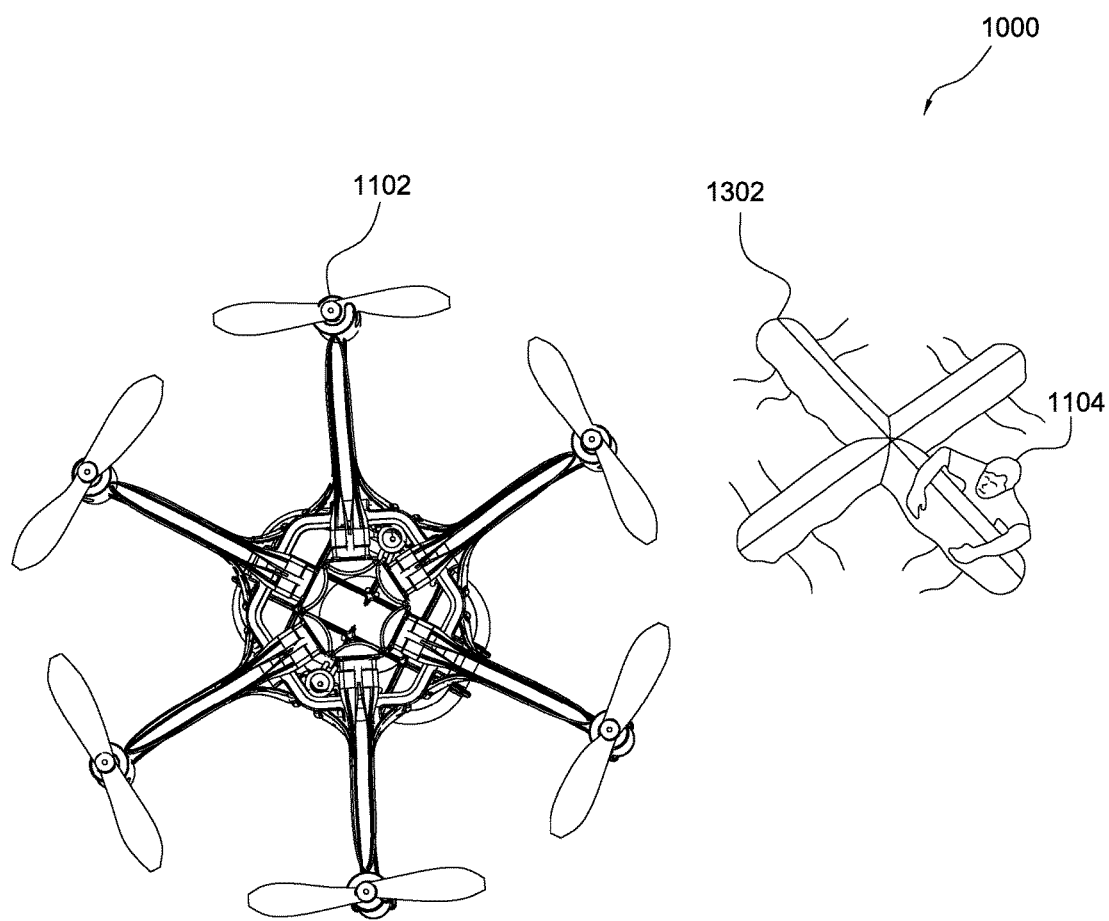
Figure 14:
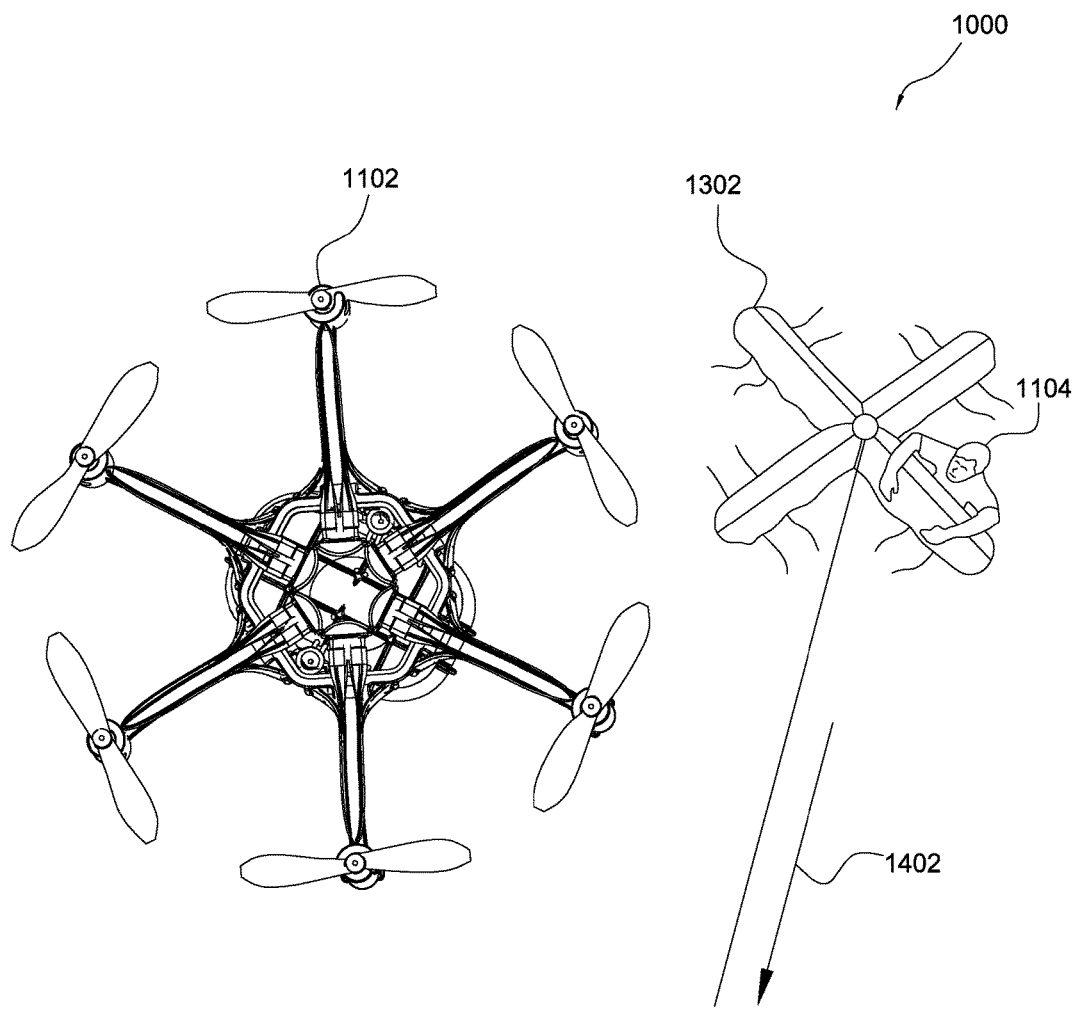
Figure 15:
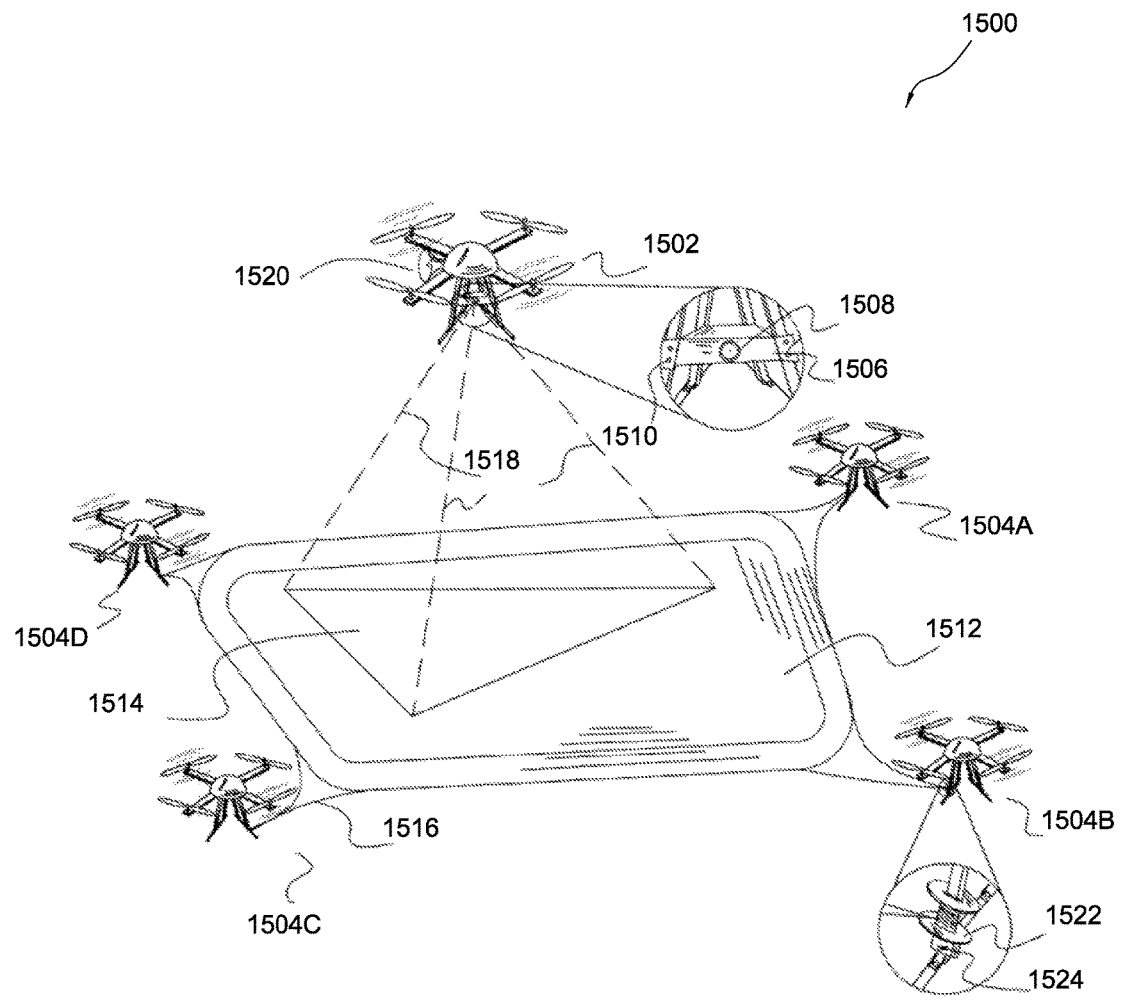
FIG. 15 depicts an alternative embodiment of the present invention in operation.

Referring now to FIG. 10, a system 1000 is shown utilizing the features discussed above associated with a ship 1002 having different locations for drone takeoff and cameras 1004. The proposed drone system includes three major components: a drone carrying a lifebuoy payload, a housing for the drone (Hive) on the deck of the ship, and multiple cameras including infrared and visible light cameras placed on ship structures that detect areas 1006 around proximate to the ship. As shown in FIG. 11, a drone 1102 is deployed to rescue person 1104. A camera 1106 is utilized to provide the user with images of the party, and a payload 1202 carried by the drone 1102 is deployed to the party 1104, as shown in FIG. 12. In one embodiment, the payload could include an inflatable device having a plurality of arms 1302 for the party to float on, as shown in FIG. 13. The floatation device could be secured to a towline 1402, which in turn tows the party back to the ship.

The detection of MOB is achieved primarily via computer vision through infrared and visible light cameras. When the man-overboard warning is triggered, the drone with the payload will take off from the hive and fly over across the sea to seek the MOB with its own onboard infrared camera. The process is fully automated, but could accommodate commander intervention. After the MOB is located, the drone releases its payload (a lifebuoy, a thermal unit and etc.) to the MOB. Once this rescue procedure is finished, the drone will return to the hive automatically and recharge itself before the next rescue mission. It is recommended that for a ship size like a destroyer, at least four such units be strategically placed on the ship.

The Drone and the Payload

A multicopter (e.g. a quadcopter, a hexcopter and an octocopter) has been proven to be a reliable and easy-to-control small-scaled airborne platform. Battery powered multicopter has been widely used in personal and commercial applications in recent years. Large octocopters (such as DJI's S1000) can fly for more than 20 to 30 minutes in a single charge while carrying a payload of more than 8 pounds. We are proposing a similar multicopter drone with a maximum speed of 40 mph or 34.7 knots and a radius of operation of at least 2 nautical miles. The drone is capable of auto-piloting such that that it can take-off, navigate to the desired location, search for the MOB and return without any human interactions. With a payload of at least 8 pounds, the drone can carry various rescue equipment including but not limited to lifebuoy and MK6 float smoke. The drone is equipped with high definition visible light camera and infrared camera, which can detect the MOB in water during day and night. The drone is built in an IP 67 enclosure that provides enough protection against temporary water immersion. The drone has the on-board self-diagnostic capability to minimize the maintenance procedure.

The Housing of the Drone (the Hive)

The housing of the drone or the so-called 'Hive' is the droneport to store, reload the payload, and recharge the drone between operations. In a ship of a destroyer size, we place four such hives on the decks of both the port and the starboard side. Typically infrared cameras are placed close the hives. Additional standalone infrared (IR) camera sensors could be placed around the ship to look out at sea; for instance, a standalone IR camera could be placed at the stern position. The hive consists of two parts: the upper part is a hangar to store the drone, and the lower part is where all the electronics are located. The hangar is covered with an automatic retractable dome-shaped hatch, which will open during the take-off and landing of the drone. It is closed during other times to protect the drone. There will be a charging pad at the bottom of the hangar to charge the battery of the drone during the storage as well as the locking mechanisms to fix the drone after landing.

The ground station for the drone is located in the lower part of the hive, which will communicate with the drone during mission if needed. The charging circuitry is also inside the lower part with other necessary electronics. Multiple pairs of visible light and infrared cameras are positioned strategically on the ship structure, pointing at the sea to monitor any overboard event and to provide the initial estimated position of the event. There will also be an optional IR beacon outside of the housing in order to guide the drone during the self-landing when GPS signal and communication is not available.

Detection and Searching

The MOB has to be identified and tracked both quickly and accurately. To accomplish this task automatically, we rely on passive infrared cameras and computer vision (CV) algorithms that are deployed on both the ship and the drones.

The reason for adopting infrared cameras is twofold: 1) military applications usually require a certain level of "emissions control" or EMCON, making the use of passive detection a preferable choice. 2) human has a body temperature that radiates at the wavelength of 12 um. Long-wavelength infrared (LWIR) cameras that are sensitive to infrared wavelengths around 8-15 um can thus be used to create high contrast human body images (e.g. FIG. 1) again background seawater. Such strong contrast is welcomed for our algorithm to detect and capture an MOB incident quickly and accurately.

Specifically, the object identifying and tracking problem using CV has been extensively studied for many years. A general framework for such a task, consists of four steps: object initialization, appearance modeling, motion estimation and object localization. By applying image filters and feature detection algorithms such as the Canny edge detector, the high intensity region that represents human body in the IR camera images can be easily extracted to achieve object initialization and appearance modeling. Following that, motion estimation and object localization can be accomplished by the widely used "mean-shift" algorithm [10] to identify and track MOB events.

While there have been attempts to commercialize such an automatic MOB detection scheme with an on-ship detection system, our system stands out with the concept of "3D" detection and tracking. With the aid of the moving lifeguard drones, we introduce another degree of freedom in time and space domains to track the MOB after the falling incident occurs. Such design considerations make our system more effective and more reliable as explained in more details below.

To enable such a "3D" scheme, we apply the IR tracking at 2 places. First, multiple infrared cameras are installed on carefully selected locations on the ship to prevent any blind spots. The cameras continuously monitor a contiguous water surface extending from the waterline of the ship. The detection range depends on the image size and lens choices. As an example, for a commercially available LWIR camera with a 640×480 pixels image size and a 65 mm lens, the maximum identification range (i.e. the range that still clearly identify the characteristics of the object) can be as large as 435 meters, which is sufficient to cover the water surrounding the entire ship. The computers connected to these IR cameras continuously apply the tracking algorithms to the acquired images to look for the region with the highest correlation with the thermal features of human—this is called the "detector" mode.

If the correlation is beyond a certain threshold, the computers declare an alarm and switch to the "follower" mode. In the "follower" mode, the computer calculates the position of the target relative to the center of the frame and adjusts the cameras to re-lock the target in the center of the frame. The reason we require the target to be in the center is that the optical lenses usually have the least geometric distortion in the center, so we can be sure that the camera is pointing in the direction of the target. Therefore, the relative location of the target to the vessel as well as its absolute GPS location is known through geometric measurement before dispatching the rescue drone. To further assist the geometric measurement to pinpoint the MOB, the algorithm takes into parameters such as the GPS locations of the cameras, multiple images acquired through multiple cameras from different moments, and reference frames. Triangulations plus other standard photogeometric algorithms can be used. The GPS location of the MOB is to be fed to the drone as a waypoint for drone to home in on the MOB.

Second, an infrared camera is mounted on the gimbal system of the rescue drone. When the drone is launched, its camera is initialized to point to the direction of the target located by the on-ship infrared cameras, as shown in FIG. 4. Note that the camera starts with a wide viewing angle to ensure the target is in the field of view and then zoom in to a relatively small view angle once the target is locked. A tracking algorithm is used to calculate the position of the target relative to the drone. The algorithm is similar to what's used by the IR camera on the ship.

Subsequently the computer directs the drone to the target and also controls the gimbal system to balance for any undesired movement of the drone. As the drone flies closer to the target, the camera tilts more straight down. When the camera is almost pointing straight down, it means that the drone is roughly above the target. Then the gimbal system will lock the camera to the straight down position and the controller only adjusts the drone to track the target. Now the field of view effectively becomes a 2D coordinate system. Once the target is at the center of the frame, it means that the drone is exactly above the target and the lifesaving toolkit would then be released. Note that during the whole procedure, the drone is fully autonomous—no communication link is necessary between the drone and the ship.

The initial location estimation from the on-ship camera is passed to the drone at the time of take-off. However, if the system is operating under Non-EMCON mode, and real-time monitoring is desired, a radio link is available for two-way communications between the ship and the drone during the search and rescue phase. Furthermore, radar is another complementary option for increasing the accuracy of detection and locating of an MOB under this Non-EMCON mode.

Rescue

Rescuing is performed once the MOB has been identified. The cruise height of the drone while during searching is generally under 300 feet, which takes into considerations of camera range and ship clearance. The hover height once the drone reaches the location of the MOB is about 10 feet for accurate delivery and safety. The drone could optionally carry a mega phone and a microphone/loudspeaker device to talk to the MOB. The payload has a door at the bottom of the payload pod. When the door is opened by the control software, the content inside the payload pod is released. There is also a pushing mechanism inside the pod that helps the content come out.

The floatation device is specially designed to fit the needs for MOB. The choices of color, material, shape, as well as inflation mechanism are carefully considered to fit the hostile ocean environment. In some embodiments, some level of mobility and intelligence could be built into the floatation device. For instance, a small battery and propeller along with computer vision on the floatation device could be expected to sail toward the MOB after being release onto the water, thereby greatly enhances the chances of being grabbed by the MOB. In addition, we will be developing the floatation device to behave like a mini robot for rescuing unconscious MOB.

In order to save one MOB, all the drones could be optionally dispatched in tandem or simultaneously to increase rescue success rate. Each drone might carry different payloads. For instance, a thermal unit could be dropped to fight hypothermia After the MOB has taken hold of the floatation device, the drone has two options: either it hovers above the MOB to give a clear indication of the whereabouts of the MOB for further retrieval, or it returns to the ship, with the information of the GPS location of the MOB.

Two types of retrieving methods can be used right after the MOB is stabilized. One method is to sail the ship back to the proximity of the MOB and retrieve by conventional method. Not only does it pose danger for nearby ships and the MOB, it also interferes with the ship's planned mission. Sometimes it's not even possible in a battlefield.

To overcome these challenges, we propose another "active" retrieval method, again enabled by the used of the drone. Please note that the newly proposed method is entirely optional which has no impact on the main mission if not adopted.

We fit a spooled lifeline into the drones' payload. The lifeline could be made of standard big game fish fishing line, such as fluorocarbon leader with 200 lbs strength. The weight and the size of the spool of fishing line are well under the drone's capacity, even if the length of the fish line is over 1 mile. One end of the fishing line is tied to a reel that is fixed on the ship. The reel is not making any rotation at this stage. The entire spool of the lifeline is being carried inside the drone's payload while flying. The spool rotates freely inside the drone's payload and the lifeline is extended by the tension between the fixed reel on the sip and the movement of the drone (or by a small motor on the spool). Upon arrival at the MOB site, the drone hovers above the MOB. The spool's rotation is locked and ceases to rotate, and then the entire spool is released from the drone's payload to the MOB under. An integrated design is to tie or fasten this spool with the floatation device mentioned before.

The spool is being connected to the reel on the ship by the fishing line. Now that the MOB gets hold of the spool it signals the start of the actual retrieval. The reel onboard the ship starts reeling in the fishing line. In most cases, the ship does not need to make the dangerous and costly maneuvering to get to the proximity of the MOB. In the past the lifeline has to be cast at the MOB, which is inaccurate and very limited by throwing range. Now with this fishing line delivered by a drone technology, it becomes feasible to retrieve an MOB hundreds of yards away with ease, much like reeling in a motionless fish, as shown in FIG. 7.

The reels on board the ship are located on the drone housing or other convenient locations on the ship. The reels are much like the power fishing reel.

Design Considerations

1. Radio Transmissions:

With the understanding of minimizing radio emission for this system in times of need, we designed two kinds of modes: the default EMCON mode and the optional Non-EMCON mode.

The ship commander could switch between the two modes. For the default EMCON mode, the detection is passive, and relies on infrared imaging detection and homing. Once the drone is airborne, there is no direct radio link between the drone and the ship.

In the optional Non-EMCON mode, the detection could be enhanced by adding other active detection methods. For instance, the sailor may have a wearable which could detect contact with sea water. The wearable would also transmit GPS location for accurate search. The wireless link between the airborne drone and the ship could be utilized. The airborne drone sends live video back to ship commander for situation awareness. Optionally the drone could be operated by human besides its auto-homing capabilities, either though the video feed from the drone's camera or from line of sight of the operator. The commander is able to talk to the MOB during rescue via the megaphone onboard the drone. Radar technologies could be used to assist searching and homing.

2. Wearable Device for Sailors (Optional):

In the Non-EMCON mode, a wearable radio transmission device is carried by every crew member. It could be a necklace. The built in sensor could detect seawater contact thereby send SOS signal along with the GPS location to our system. An on-duty system admin could further determine if the situation warrants further action. This necklace would also be able to track every crewmember on a real time basis no matter where they are in the ship.

3. Floatation Device and Payload:

Flotation devices will be designed for the purpose of the system. The objective is to make the floatation device as easy to grab as possible by the MOB, and still could be fit in a standard payload pod. The floatation device is an automatic inflatable tube. There is a water sensor, which upon coming into contact with water would trigger the release of compressed $CO_2$ that is stored inside a canister. The $CO_2$ gas then fills the sealed tube within seconds. The inflated shape would resemble a '+' sign with dimensions of 10 ft. by 10 ft., and there are handles on the tube. Dozens of 2-foot lines would be attached to the tube for easy grabbing.

The drone and payload system is like a Swiss army knife in that it can carry and drop any item. Each payload is a preloaded pod that can be swap in and out of the drone in seconds even by untrained personnel. For example, in order to fight hypothermia, a chemical or electrical thermal unit could be put inside the payload. Sea dye marker could be another choice. Other payloads could be medicals, radios, small weapons and etc. Different types of payload could be stored on ship. With different situations, the payload could be snapped on or to be reloaded after a drone comes back to its housing.

4. Weather Resistance:

Our drone is designed as an all-weather flying machine. Weather resistance design is one of the key areas of our effort and expertise. Our design of the drone has much improved aero-dynamic, flight control stability and weight distribution. In addition the choice of hexcopter or octocopter makes it more wind resistant with extra battery power. The electrical and mechanical parts such as batteries, controllers and motors will be waterproof to an IP67 level. In the future roadmap, our drone would be able to land on water with its own buoyancy.

5. Operating Safety:

Our drone has built in collision avoidance capability based on omni-directional computer vision. It also has geo-fence to avoid the known no-fly zone. For instance, the drone will avoid the collision with the body of the ship itself. The launch command could also take into the helicopter information so that when a helicopter is active the drone operation will take a special sequence of approval process to fly a mission. In designing the software we also build in artificial intelligence for the drone to forecast and recognize potential hazards on its flying path.

MOB is a serious problem for ships, commercial vessels, oil platforms, ferry boats, and fishing boats. To illustrate the severity of the MOB problem, the ferry boats tragedy in South Korea in 2014 claimed about 300 lives. Based on industry statistics, on average over 20 passengers and crews of cruise and ferry ships became victims of MOB. Many more unreported incidents would make this MOB problem even more pronounced. In the US, the fatality rate of MOB occurred in boating is over 50%.

Our system could be used by civilian ships to greatly enhance the effectiveness of detection and rescuing MOB.

FIG. 10 depicts an alternative embodiment of the present application. The overall scenario of projecting images and broadcasting sound in midair is illustrated in 1500.

In the exemplary embodiment, a drone 1502 carrying a speaker 1520 and a projector 1506 is shown airborne. The projector 1502 is fastened to the drone by fasteners comprising 1510. The lens 1508 of the projector 1506 projects an image 1514 onto a screen 1112 as illustrated by beam of light 1518 emitting from the lens 1508. The four corners of the screen 1112 are fastened by tethers and spread by four airborne drones 1504A, 1504B, 1504C and 1504D. As depicted, one or the tethers 1516 is connected to the corner of the screen 1514 and a drone 1504C. Drone 1502 is referred to as "Projecting Drone" (or "PD"), while drones 1504A-1504D are referred to as 'Screen Spreading Drone", or SSD.

In some embodiments, the tether 1516 is fastened directly to a drone such as 1504A, while in some other embodiments, the tether 1516 is connected to a reel onboard a drone. The reel could be driven by motor or spring to exert tension on the tether. Identifier 1522 illustrates the reel and identifier 1524 illustrates the motor, both of which are mounted on the frame of an SSD 1504B. In some embodiments, the drone has sensors to measure the tension on the tether, and the drone controls the motor to loosen or tighten the tension.

There are a variety of other embodiments that utilize some parts or all of the above elements and configurations. In one embodiment, the drone 1502 has an integrated video projecting function, which allows it to project video images without a dedicated video projector.

In another embodiment, the video images are projected onto a natural or man-made surface, still or moving. For example, the surface of a building, a structure, ground, the surface of a moving object or objects such as a blimp, aircraft, another drone, vehicles.

In yet another embodiment, the drones that spread the screen 1112 need not be four, but could be any other numbers. The place where the screen is attached to the drone need not be at the corner, it could be any part of the screen, for example, the center of the screen. In Yet another embodiment, only a portion of the screen is attached to at least a drone and other portions are attached to other objects, for instance, the ground. In this case, the screen is spread by the forces of the at least one drone while a portion of it is fixed by the ground.

There is no special requirement of the shape, geometric form, material, and configuration of the screen 1112. Any surface that can reflect light would be considered as a screen. In one embodiment, the screen is made of a piece of fabric, in another embodiment, the screen is the outer surface of an enclosure in which air is pumped, such like an air balloon.

The screen 1112 is made of material that is able to reflect light or intercept light, such as but not limited to fabric, paper, rubber and etc. It could be flexible or rigid.

In some embodiments, the drones 1502 as well as drone 1514A-1514D have sensors to stabilize the instruments carried by them, using devices such as gyroscopes. It is sometimes important to stabilize the video images projected by the PD due to the influence of airflow and drone's own motions. Gyroscope is a widely used tool to obtain stability, which could be used in achieving stability of the light projected. Another way to enhance stability of projected images is to achieve relative stabilities among the PD and SSDs. The PD and the SSDs communicate with each other about its relative position with the rest of drones. Adjustment is made by a drone when there is a deviation from previously stable positions vis-à-vis other drones.

In some embodiments, the drones 1502 and drone 1514A-1514D are controlled remotely, or by their own onboard communication and control modules for concerted movements. Yet in some other embodiments, part of the screen is attached to other objects such as the ground or a structure, while part of the screen is tied to a drone a group of drones.

In some embodiments, the source of the video or audio is from received as wireless signals. Yet in other embodiments, the video or audio source is from an onboard camera and microphone/loudspeaker device, or from onboard storage medium carried by the drone 1502. Yet in some other embodiments, the video and audio sources are from the combination of the above sources.

In one embodiment, only the drone with a speaker is used to broadcast audio to the surrounding environment. In another embodiment, only the drone with image projecting capability is used and the images are projected onto existing natural or man-made surfaces. Yet in another embodiment, only the apparatus with the screen spread by drones is used to reflect or to display images, which come from a light projecting source, such as a fixed projector. There are other possible configurations using the different parts or all the elements mentioned above in yet other embodiments.

Figure 16:
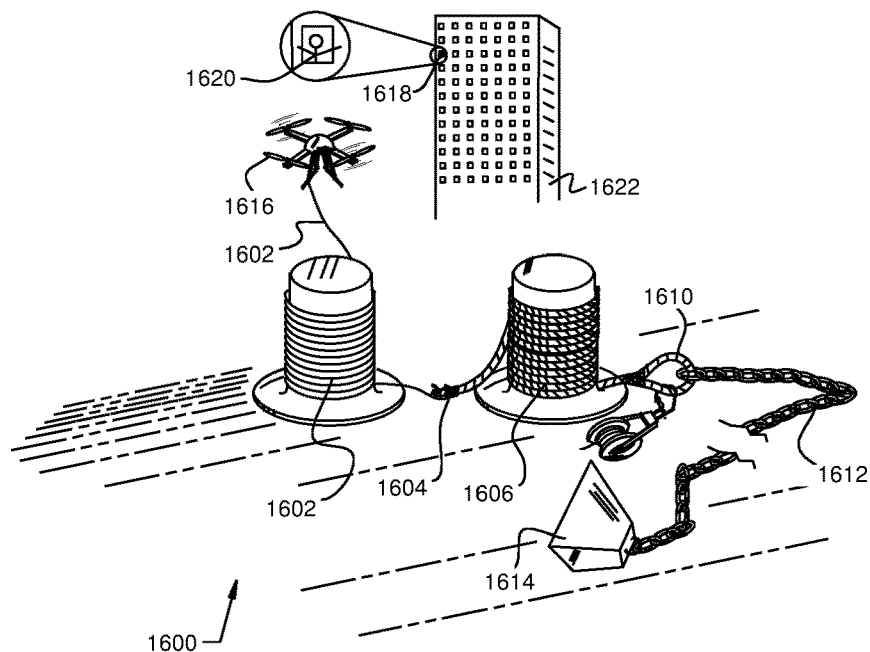
FIG. 16 depicts a drone flies with the segment with lower breaking strength of a GST to a target location.

FIG. 16 depicts a drone flies with the segment with lower tensile strength (sometimes called 'breaking strength') of a GST to a target location. The drone is flying with the less sturdy segment of a GST 1602 attached to it, and is heading for the target location 1618 to deliver a desired object 1614, as illustrated in 1600. The drone 1616, in this case a quadcopter, is flying in midair. The lower breaking strength end portion of the GST 1602 is attached to the drone 1616. The rest of the 1602 is spooled atop ground. It is connected at junction 1604 with a gradually sturdier segment 1606. In this embodiment the segment 1606 is made of a rope or cable. The other end portion of the rope 1606 has been made a loop 1610 and is connected to a metal chain 1612 at 1610. In addition, a pulley 1608 is also attached to the GST at the end portion of the rope 1606. in some embodiments, the pulley 1608 is a power reel that can reel the lines. The metal chain 1612 is further attached to an object 1614, which is desired at the target location 1618. The target location 1618 is located at the $20^{th}$ floor of a high-rise building 1622. A person 1620 is ready to get hold of the drone 1616 and the attached GST. Either the person 1620 or someone else could control the flight of the drone 1620. In one scenario, the person 1620 could send the drone from the target location 1618 and let it fly to the ground, and someone on the ground could fasten the GST to the drone.

Once the person 1620 gets hold of the drone 1616 and the attached GST 1602, the person could start pulling the GST either by himself by a machine. The pulley 1608 would be sent to the target location for the person 1620 to use. The pulley 1608 could be replaced with a machine involving a pulley or a reel. The person would be able to eventually get hold of the desired object 1614, which typically would be too heavy or inconvenient to deliver to the target location with other means.

The drone needs to afford the weight of the portion of the GST between the target location and the point where the GST first gets support from the ground or a structure. Further the breaking strength of the portion of GST that is at the target location needs to be greater than the weight of the portion of the GST between the target location and the point where GST first gets its support from the ground or a structure.

Sometimes a segment of the GST itself is the desired object. One example is mooring a vessel at a dock, where the mooring chain is the desired object to be delivered to the dockside and to be secured on a mooring post.

Figure 17:
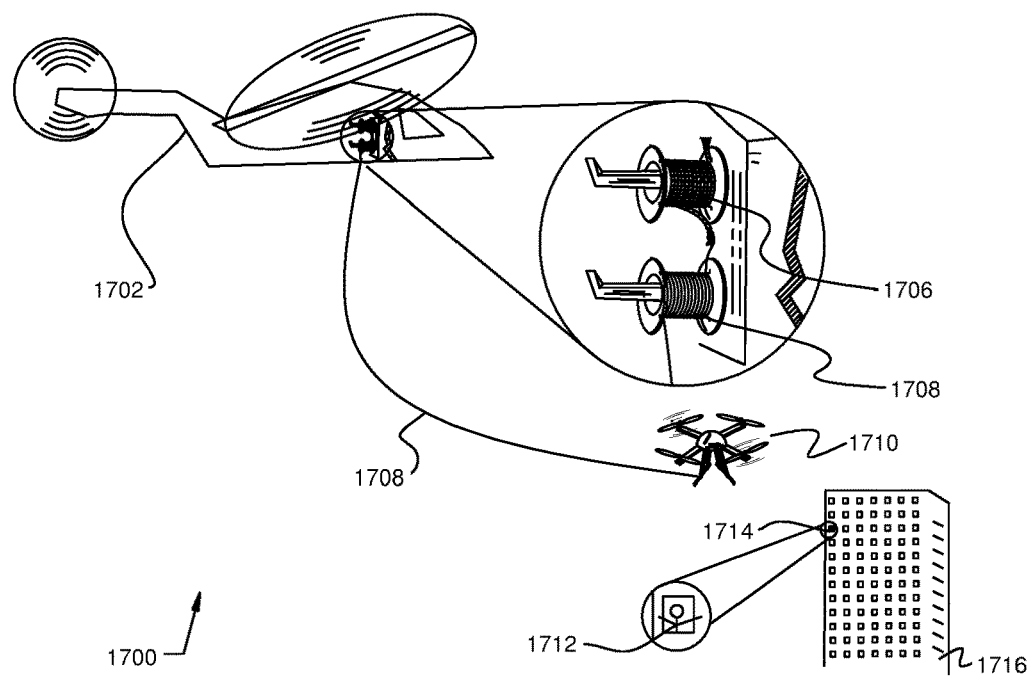
FIG. 17 depicts an apparatus being used by a helicopter.

Please refer to FIG. 17, which depicts the apparatus being used by a helicopter in mid air. In 1700, a helicopter dropped an embodiment of the invention and attempts to establish a connection with a target location that is not directly under the helicopter. The helicopter 1702 initially stores the embodiment of the invention. It flies in midair and then drops the drone 1710. The drone is attached to the less sturdy end portion of the GST. The GST consists of the tether segment 1708, which is the less sturdy segment, and 1706, which is the sturdier segment. Both 1708 and 1706 are spooled inside the helicopter 1702. The drone flies to the target location 1714, which is at a certain floor of a building 1716. A person 1712 is at the target location 1714 to get hold of the drone 1710 and the GST. Once the person 1712 gets hold of the drone 1710 and the end portion of the GST 1708, he starts pulling the GST so that the sturdier portion 1708 could be reached, which would allow a sturdy connection being established between the helicopter and the target location.

Figure 18:
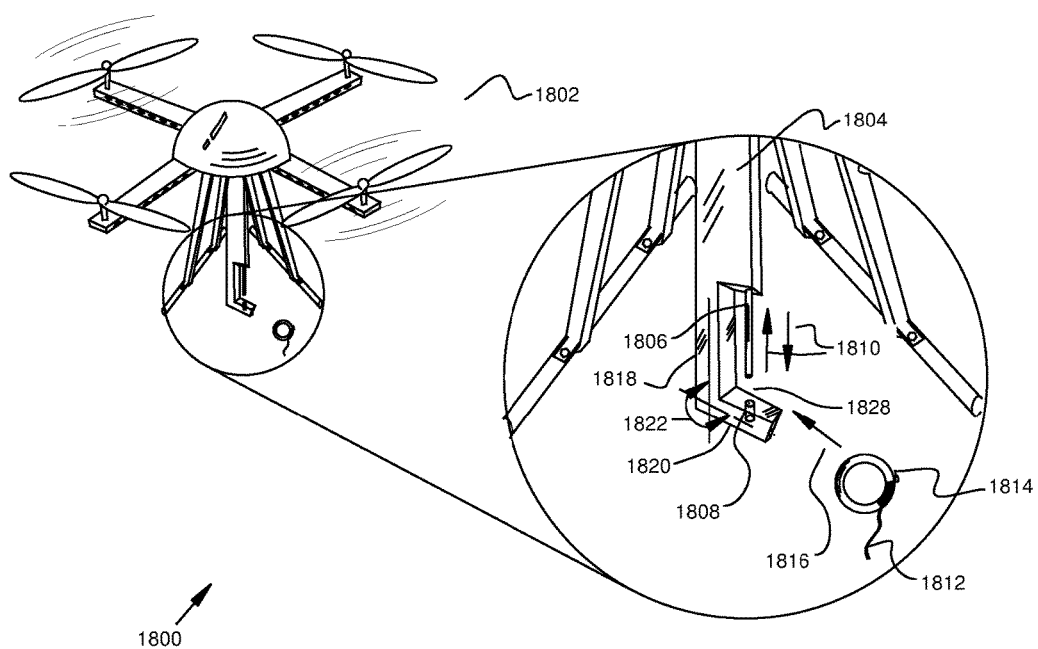
FIG. 18 depicts an embodiment that has auto release mechanism for the tether to separate from the drone.

FIG. 18 depicts an embodiment that has auto release mechanism for the tether to separate from the drone. When the drone needs to release the tether, a linear actuator as depicted in FIG. 18 moves to let the tether go free. 1800 is one example of auto release mechanism and there are a number of other possible ways to accomplish the auto release functionality. The drone 1802 has a structure 1804 underneath its belly, which houses the linear actuator. The actuator is controlled by a micro controller on board the drone. The moving arm or the thrust rod of the actuator is shown as 1806, which can move in two directions as depicted in the two arrows as in 1810. When the moving arm 1806 moves down, it moves all the way down to the bottom of a small hole 1808, which is situated in the fix lower arm 1820 of the structure 1804. A tether 1812 is first fixed in a tether terminator, which in the figure is the ring shaped terminator 1814. When the moving arm 1806 engages with the hole 1808, an enclosure is formed by the moving arm 1806, upper arm 1818 and the lower arm 1820, so that the tether terminator 1814 is locked inside the enclosure. When the moving arm 1806 lifts and disengages the hole 1808, an opening 328 is made to allow the tether terminator 1814 to release from the opening 328 and be separate from the drone 1802.

When the tether is to be connected to the drone, the tether terminator 1814 is inserted into the opening of the enclosure for the moving arm 1806 to lock the ring, as shown in the direction 1816. The moving arm 1806 moves down inside the ring 1812 and into the hole 1808, thereby locks the tether terminator 1814. The arm 1806 is also able to move upward so that an opening is created between the moving arm 1806 and the lower arm 1820, which will allow the ring and the tether to go free.

In some embodiments, the structure 1804 is extendable downward like a telescopic antenna when the drone is in midair. This extension will give the drone the ability to capture a tether in midair with the help of the actuator. It becomes an extendable hook with automated closing arm 1806.

The upper arm 1818 and the lower arm 1820 connect with each other at an angle between their respective longitudinal axes, as shown in 1822. In order for the tether terminator 1814 to exit the opening quickly, the angle is less than 270 degrees.

Figure 19:
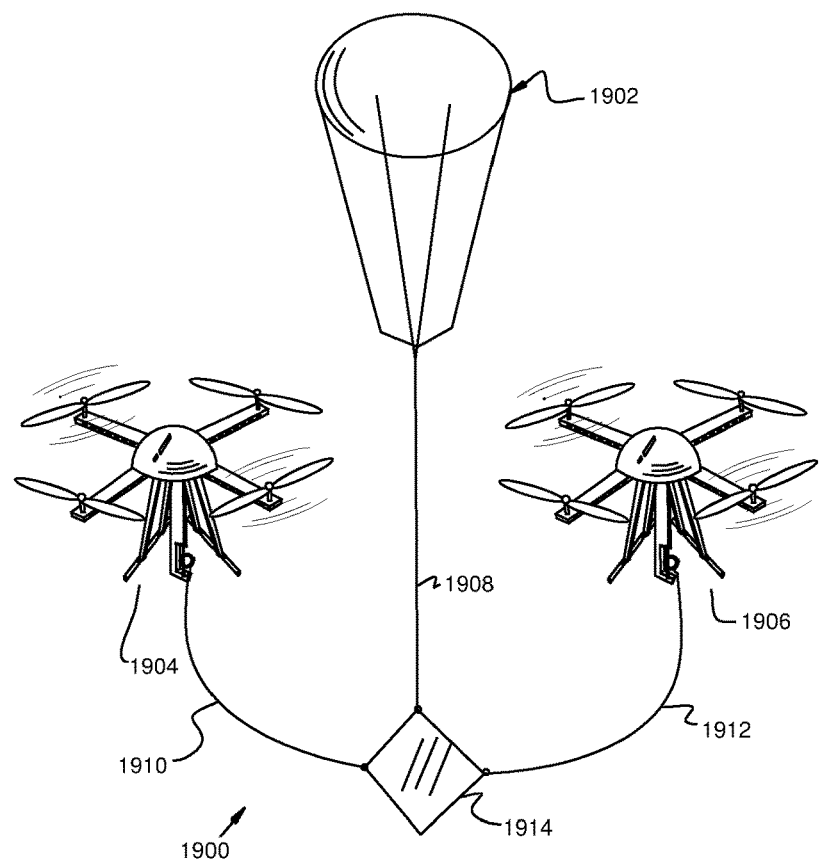
FIG. 19 depicts a drone being connected with a tether adjusting a mirror's position in midair.

FIG. 19 depicts a drone being connected with a tether adjusting a mirror's position in midair. 1900 illustrates the overall method of moving a heavy object which is largely supported by an airplane, a helicopter or a balloon. Drone 1904 is connected to a tether 1910, which is in turn connected to an object, in this case a mirror 1914. The mirror 1914 is lifted by a balloon 1902 through a cable 1908. In order to adjust the mirror more accurately, another drone 1906 and another tether 1912 being connected to the drone 1906 are used, and the tether 1912 is connected to the mirror 1914. The balloon 1902 provides the heavy lifting needed by the mirror 1914, while the desired angle and position of the mirror 1914 are adjusted by the drones 1904 and 1906.

The system is useful when there is a need to reflect laser beams in midair. For example, some weapon system shoots laser beams at enemy target, but due to the earth curvature, and the fact that a laser beam cannot bend its path, such laser is limited to target with line of sight. This novel reflective system is able to reflect laser at an altitude to redirect the laser beam at enemy target out of the line of sight. It is easy to see that the mirror could be replaced with other objects, such as a cutting tool, a weapon, a piece of communication equipment, a reflective device, an energy source, and a solar panel. For instance, a high energy laser system could be carried by the balloon in midair, and the drone could be used to direct the laser from the laser weapon at enemy targets. There is virtually no recoil force from such a laser weapon and that makes this laser system powerful. In addition the laser is beamed down from an elevation which also makes it very desirable in battlefield.

An air balloon or an aircraft is able to hang a piece of heavy equipment with a cable or a tether. But it is hard to adjust or control the position and orientation of that piece of equipment because the tether or the cable is flexible. A drone or a group of drones are able to create enough torque to accomplish just that.

There could be numerous other objects that could be used in the place of the mirror 1914 as illustrated in 1900. The tether 1908 used by the balloon 1902 is generally sturdier and heavier than the tether 1910 connected directly to the drone 1904 and the tether 1912 connected to drone 1908. The tethers could be viewed as a variation of a GST.

The balloon could be replaced by a different type of aircraft such as a helicopter, or a projectile. Another scenario is that the object 1914 could be lifted by a crane, and the drone 1904 is used to tweak the position of the object 1914. Even a heavy weight object 1914 could be moved when it is suspended in midair by a drone, especially if the movement is rotating around an axis close to the center of the gravity of the object 1914. In most cases, the object 1914 weighs over 10 pounds.

Figure 20:
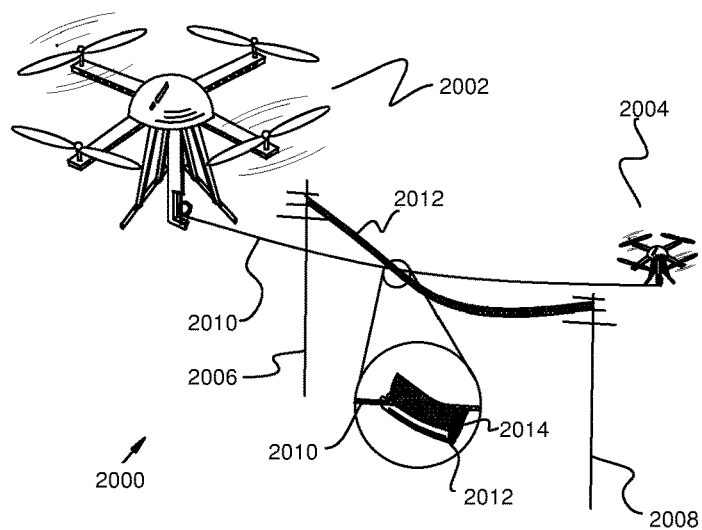
FIG. 20 depicts a drone being connected with a tether clearing out ice and snow accumulation with the help of another drone.

FIG. 20 depicts a drone being connected with a tether clearing out ice and snow accumulation with the help of another drone. The accumulation clearing action is captured in 2000. Snow and ice accumulation is a well-known hazard to overhead cables. The novel solution provided in FIG. 20 employs a drone 2002 and another drone 2004, connected by a tether 2010. Two power line poles 2006 and 2008 support an overhead cable 2012. Snow and ice accumulation is shown in 2014. The drones 2002 and 2004 move along the length of the cable 2012, so that the tether 2010 could press against the accumulation and the cable 2012 and scrape off the accumulation 2014. The operation could be automated because the path of the cable is known. It could also be monitored by the cameras carried by the drones 2002 and 2004.

In a slightly different version not illustrated here, the drone 2004 could be replaced with a object providing weight, which would force the tether 2010 to bend at an angle at the point where the tether is in contact with the cable 2012, the drone 2002 could drag the tether 2010 along the length of the cable 2012 to scrape off the accumulation.

Further, the scraping could be enhanced using an electrical heat wire or unit at the point of contact with the accumulation, provided the heat is under a certain limit not to burn the cable.

Figure 21:
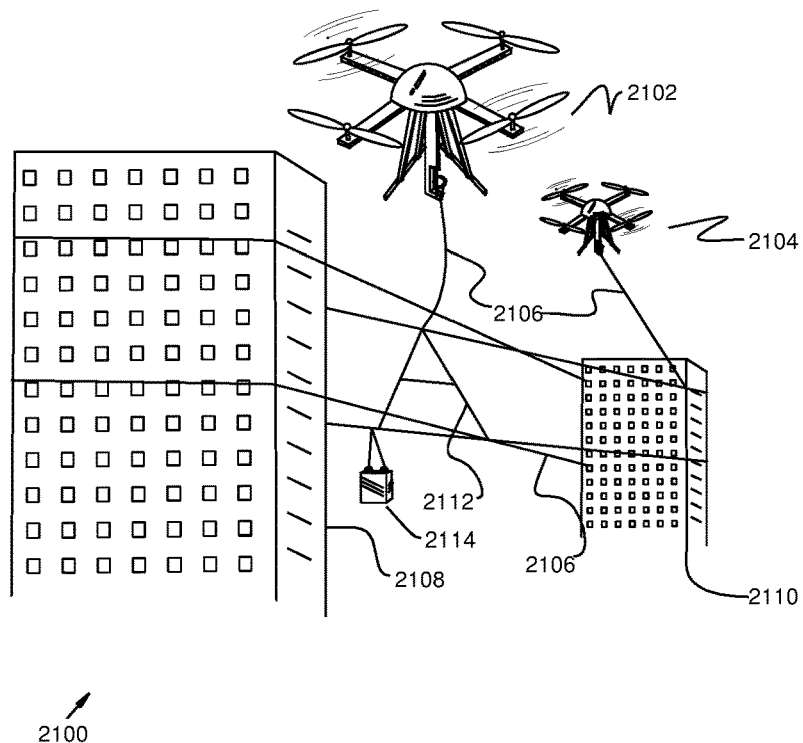
FIG. 21 depicts a drone connected to a tether making patterns using the tether, with the help of another connected drone.

FIG. 21 depicts a drone connected to a tether making patterns using the tether, with the help of another drone connected to the same tether. 2100 illustrates the pair of connected drones making concerted movements between two tall buildings 2108 and 2110 so that the tethers could form patterns. Drone 2102 and drone 2104 are connected with a tether 2106. The tether could also be bundled with lighting element such as LED light strips. The drones 2102 and 2104 could be programmed to make complicated and patterned movements. As a result of the movements of the drones 2102 and 2104, the tether 2106 would form patterns or shapes, as well as being fixed by an object. In this case, drone 2102 flies around the two buildings 2108 and 2110 several times; and then it flies between the tethers to form a letter 'A' as shown in 2112. In addition, the tethers could be used to support the weight of an object, such as an object 2114. To fix a tether to another object or another part of a tether, one technique is to let the drone fly around that object or that part of a tether multiple times so that the tether wraps around that object or a part of a tether. A knot could be formed by the tether if the drone moves in a preprogrammed path. If LED lights are bundled with the tether and power source is provided, then the letter 'A' will be lit up as a decoration or public display. In this weaving operation, at least a portion of the tether is substantially fixed relative to the objects, in this case are the buildings 2108 and 2110. Furthermore the drone could move around another potion of a tether or an object multiple times in plain or sophisticated patterns like knotting patterns, so that the tether could wrap around it to substantially fasten the tether to the object of another portion of the tether.

Figure 22:
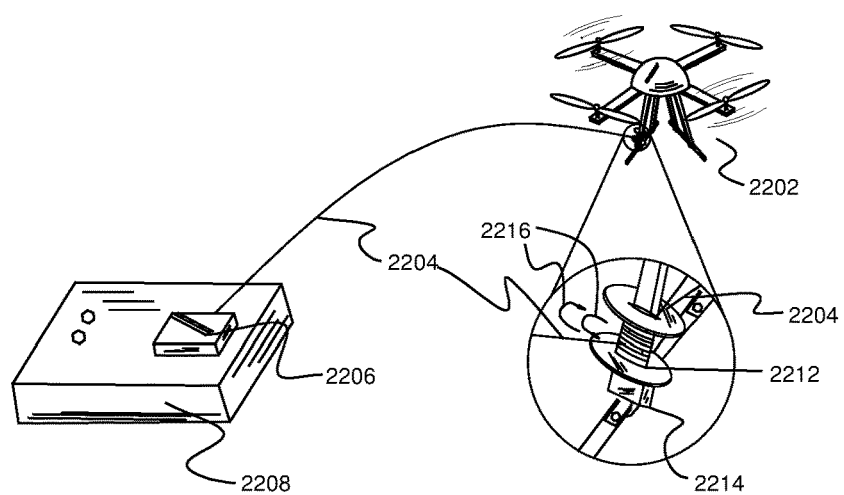
FIG. 22 depicts a retractable tether and a power recharging scenario.

FIG. 22 depicts a retractable tether and a power recharging scenario. 2200 illustrates the recharging apparatus and method. The drone 2202 is in midair. The tether 2204 is either a conductive wire itself, or a bundle of a conductive wire and a tether. The tether is retractable. A reel 2212 winds and unwinds the tether 2204. A motor 2214 enables the reel 2212 to spin around its axis in both directions as indicated by the arrows 2216. This allows the tether 2204 to extend or retract. The motor 2214 is controllable by the computer device onboard the drone 2202. The tether 2204 is connected to a rechargeable battery on board the drone 2202, which is to be recharged. The other end of the tether and/or the conductive wire 2204 is connected to a recharging device 2206. The power recharging device 2206 could be as simple as a power plug, or could be a inductive recharging device which only requires the device 2206 to be at close proximity to the charging station 2208, or it could be some other recharging device. Charging station 2208 provides the power source to recharge the batter in the drone 2202. The charging station 2208 could be equipped with power outlet or inductive charging mechanisms. The charging station could be ground based or could be based on in midair, supported directly or indirectly by another drone or another aircraft. If the charging station is airborne, then the recharging operation of the drone 2202 is analogous to refueling a fighter jet in mid air. It could provide the drone 2202 sustained ability of staying airborne.

Further the extendable and retractable tether 2204 may be connected to other devices in other embodiments. The benefits of having extendable and retractable tether is that the device being connected to the tether 2204 could be stowed away when it is not needed. In addition, it provides a means for the drone to exert force on the tether and the connected device, which enables the apparatus capable of doing a variety of jobs. One example is a tether connecting two drones each having a retractable and extendable devices installed. The retracting of the tether makes the two drones moving closer while the extending of the tether allows farther distance between them.

Further the retractable and extendable device could be used in addition to the automatic tether release mechanism described in this specification. The tether 2204 is connected to the tether terminator 1814 in FIG. 18.

The tether could be connected to a weapon, a device emitting laser, a reflective device, a power recharging device or a solar panel.

Figure 23:
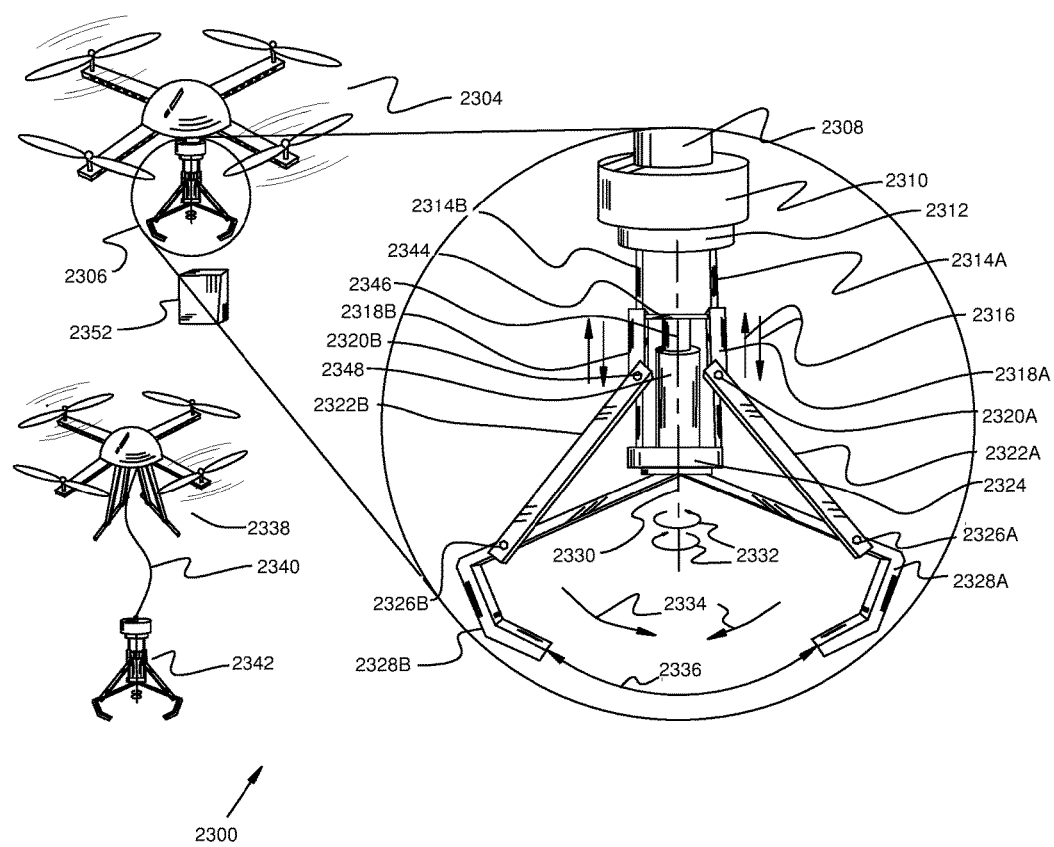
FIG. 23 depicts a gripping mechanism coupled with a drone either directly or through a tether.

Please refer to FIG. 23. FIG. 23 depicts a gripping mechanism coupled with a drone either directly or indirectly through a tether. 2300 illustrates the details of the gripping mechanism, a drone coupled directly with the gripping mechanism, and a drone coupled with the gripping mechanism through a tether. The gripping mechanism 2306 enables the drone 2304 to get hold of an object and manipulate the object. The gripping mechanism 2306 could be mounted on any side of the drone 2304, like up, down or sideway side of the drone 2304, sometimes with the help of the mounting rod 2308, which could be in different length or orientation with respect to the drone 2304's body. FIG. 8 only shows one possible mounting position for the gripping mechanism. Object 852 is to be gripped or grabbed by the fingers 2328A and 2328B of the gripping mechanism 2306. In a different configuration, a drone 2338 is connected to a gripping mechanism 2342 through a tether 2340. One advantage of a tether 2340 versus a mounting rod 2308 is that a tether tends to weigh less, and flexible, both contribute to the stability and maneuverability of the drone, especially in the case when the mounting rod 2308 is long. However, a tethered gripping mechanism is usually under the drone, unlike a rod which can be placed above or on the side of a drone.

A motor 2310 is mounted on the mounting rod 2308, the motor 2310 enables the gripping arm and fingers to rotate around its central axis 2330, in both directions as shown in 2332. The ends of the guide rod 2314A and 2314B are fastened to the frame end members 2312 and 2324, which is directly coupled to the motor 2310. When the motor 2310 is in operation, its torque is transferred to the frame end member 2312, which in turn make the rest of the gripping mechanism rotate around its central axis 2330, in both directions as shown in 2332. This rotating motion helps the gripping mechanism overcome possible resistance from a possible attachment between the object being gripped and some other object. For instance, when the drone is used to pick fruits like apples from a tree, after an apple is being gripped by the gripping mechanism 2306, the rotating motion 2332 around the central axis 2330 makes it easy for the apple to break from its stem.

The frame on which the actuator housing 2348 is installed comprises a frame end member 2312, another frame end member 2324, and two guide rail 2314A and 2314B being parallel to each other. The guide rails 2314A and 2314B are fastened to the frame end member 2312 and 2324, and are perpendicular to the two frame end members 2312 and 2324. The housing of the linear actuator 2348 is fastened to the frame end member 2324, while the thrust rod 2346 of the actuator is able to move along the central axis 2330. The top plate 2344 is joined to the end of the thrust rod 2346. The top plate 2344 is further fastened to two moving tubes 2318A and 2318B respectively. The two moving tubes 2318A and 2318B are fitted to the guide rod 2314A and 2314B, respectively, which can move in both directions as shown in 2316 along the guide rods 2314A and 2314B. The ends of the right gripping arm 2322A and the left gripping arm 2322B are connected with the moving tubes 2318A and 2318B through rotatable couplings 2320A and 2320B, respectively. The other ends of the right gripping arm 2322A and the left gripping arm 2322B are connected to the right gripping finger 2328A and 2328B through rotatable coupling 2326 A and 2326B respectively. The movement of the top plate 2344 away from the actuator housing 2348 makes the moving tubes 2318A and 2318B move upward, away from the actuator housing 2348, along the guide rods 2314A and 2314B respectively. That motion in turn causes the up ends of the gripping arms 2322A and 2322B to move upward because of the coupling 2320A and 2320B, respectively; and causes the lower ends of the gripping arms 2322A and 2322B to move inward toward the central axis 2330, because of the couplings 2326A and 2326B, respectively. As a result of the inward movement of the gripping arms 2322A and 2322B, the gripping fingers 2328A and 2328B moves toward the central axis 2330, as shown in direction 2334. When the top plate 2344 moves down and toward the actuator housing 2348, the motions of the moving parts are reversed, resulting in the opening of the gripping fingers 2328A and 2328B, as shown in the direction of 2336. The two directions 2334 and 2336 correspond to the gripping motion and releasing motion of the gripping mechanism respectively.

The gripping mechanism is one example of a type of device for removing an object from its original place. The embodiment of the present invention enables picking up an object, especially a small object under 10 pounds from one place and place it somewhere else. It is useful in cleaning animal waste on the streets, for instance. Of course there are numerous applications that this type of embodiment could be used. It mimics a human's hand capable of flying and being controlled by a human or software.

In some other embodiments, there could be more gripping arms or gripping fingers. In addition, each gripping fingers could be move independently by using independent actuator. Such gripping mechanism would be able behave more or less like a human's hand and be able to perform a multitude of tasks a human's hand is capable of performing. There are a number of ways to make the gripping mechanism dexterous that a person with ordinary kill in the art would be able to implement.

Further, the camera on the drone could take pictures or videos. The microphone/loudspeaker device on the drone could also record the sound around the work site. The information is sent to a human or a software application, which in turn analyzes and makes decisions on the next move. The control instructions are sent back to the drone and the gripping mechanism for the next move.

Figure 24:
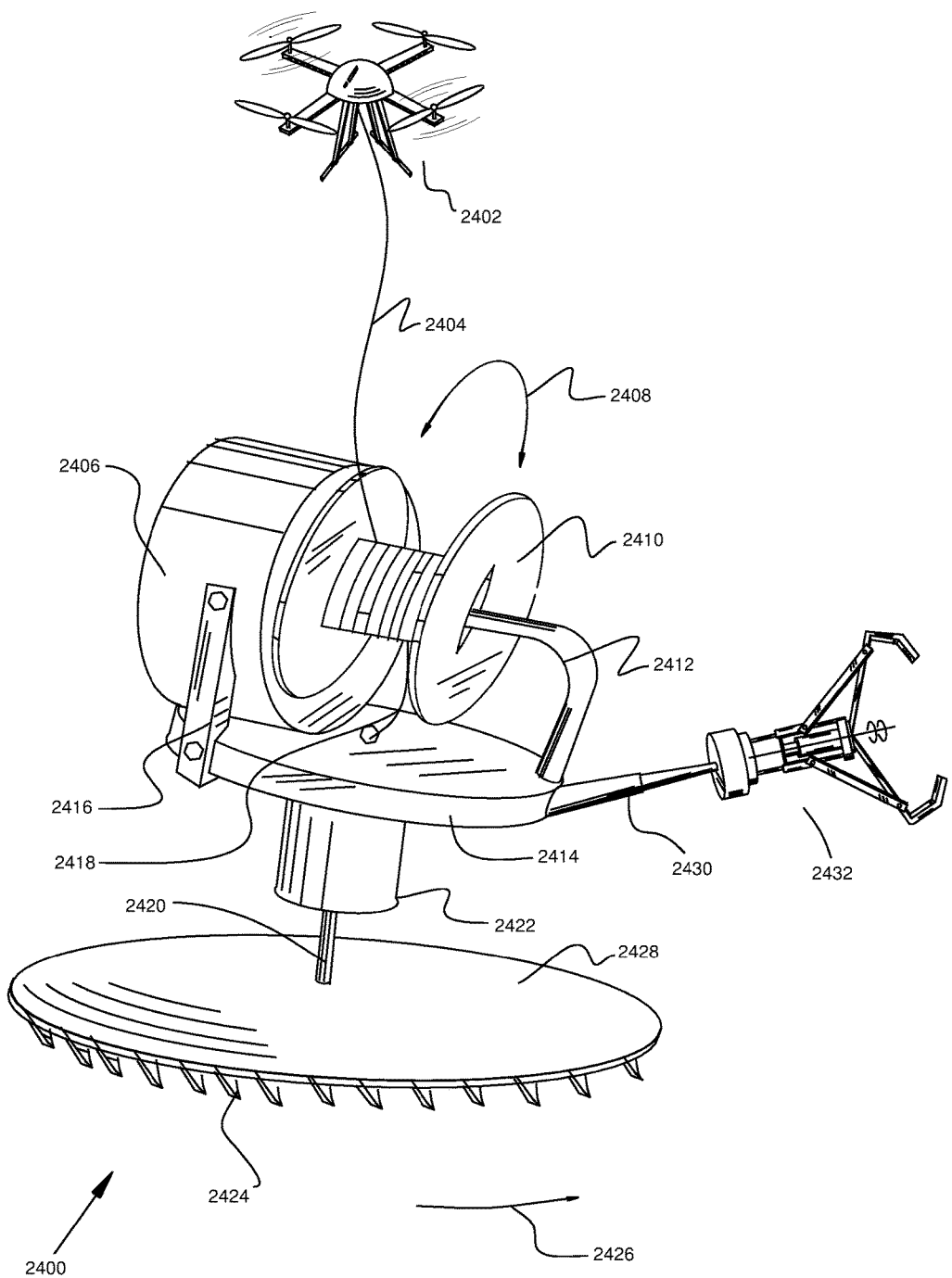
FIG. 24 depicts a drone being connected to a circular saw through a tether.

FIG. 24 depicts a drone being connected to a circular saw through a tether. A saw is designed to separate an object by removing parts of the object. The embodiment of the invention is depicted in 2400. A drone 2402 is flying in midair, which has a tether 2404 tied to its body. The tether 2404 may be conductive wire itself, or it could be a bundle of a tether and a conductive wire. The wire sends power to the devices connected to the tether, such as a motor 2406 used for turning the reel 2410, and a circular saw motor 2422. The reel 2410 is mounted on a bridge handle 2412 which allows it to spin around its central axis as shown in 2408. The motor 2406 makes the reel 2410 spin in both directions as shown in 2408. The motor 2406 and the bridge handle 2412 are mounted on a plate 2414. The reel motor 2406 is fastened to the plate 2414 through connector 2416. A conductive wire 2418 goes through a hole to supply power to the circular saw motor 2422. Alternatively a battery could be installed on the plate 2414 to supply power to the reel motor 2406 and the saw motor 2422. The saw spindle 2420 is coupled to the circular saw 2428, and its cutting teeth is shown in 2424. The circular saw spins in the direction as shown in 2426.

The tether 2404 could also help the tool 2428 to be positioned to the desired location. For instance, the UAV 2402 could move back and forth in mid air and drag the tether 2404 so that the tool 2428 could be positioned to the point it is should be. The movement of the UAV 2404 could be controlled by human through viewing images from a camera onboard the UAV 2404. Or the movement of UAV 2404 could be achieved by image tracking. The image of the tool 2428 and the desired location should coincide. If there is discrepancy between the two, then the geometric distance between then will be used as an input to guide the UAV to maneuver, so that the difference will shrink until it disappears. At that point, the tool 2428 is at the desired location.

Sometimes in order to counter the torque created by the sawing action of the saw 2428 and to have more precise cutting, a gripping mechanism similar to what's depicted in 800 of FIG. 8 is used in conjunction with the saw mechanism. 2430 is an extendable and retractable rod like an antenna whose one end is coupled to the plate 2414 and the other end is coupled to a gripping mechanism 2432. The gripping mechanism 2432 grabs the object to be sawed and the saw 2428 further cuts the object. In some other embodiments, the gripping mechanism 2432 could be replaced with other temporary means for fixing the object to be sawed, such as a strap to strap around the object to be sawed. The saw 2428, the extending and retracting mechanism comprising 2406 and 2410 for the tether, the gripping mechanism 2432, and the extendable and retractable rod 2430 could all be controlled by software, and all could be controlled remotely.

It is easy for those skilled in the art to replace the saw blade 2428 and the saw motor 2422 with a different object removing mechanism, for instance, a vacuum cleaner, a drill, a device comprising magnet or electromagnet, an air blower, a grinder, a polisher or a combination thereof. Many off the shelf products could be adapted appropriately for various embodiments of the present invention.

Further the tether could be replaced with a rigid member such as a rod or other types of structure to couple the drone with the object removing mechanism.

The reel motor 2406 and the circular saw motor 2422 are controlled by the drone or remotely by wire or wirelessly. When the reel motor 2406 makes the reel 2410 spin in one direction around the bridge handle 2412, the tether gets wound up which cause circular saw 2424 and 2422 to get closer to the drone. If the reel motor 2406 makes the reel 2410 spin in another direction, the portion of the tether 2404 between the drone 2402 and the circular saw 2428 increases which extends the reach of the circular saw 2428. The circular saw 2428 could be replaced with or be used in conjunction with other devices, such as a gripping tool as depicted in FIG. 23, a device emitting laser, a power recharging device as depicted in FIG. 22, a weapon, a drilling tool, and lighting elements. For instance, a vacuum and a circular saw would enable the apparatus to cut and clean up the sawdust at the same time.

Figure 25A:
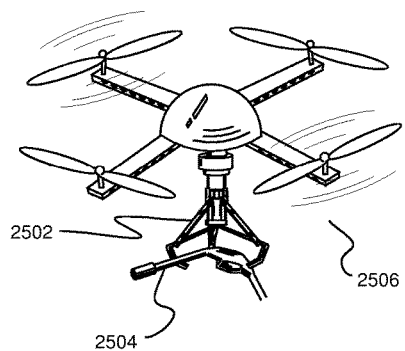
FIG. 25A depicts a drone coupled with a welding device.

FIG. 25A depicts a drone coupled with a welding device. Drone 2506 is first coupled with a gripping mechanism 2502, which is introduced in more detail in FIG. 8, and the gripping mechanism is further coupled with a welding device 2504. The welding device joins two objects that are separate form the embodiment of the invention by heating and melting the parts of the two objects where the joining happens. There could be many other devices that would achieve the purpose of joining two objects, such as a nail gun, an adhesive dispenser or stapler. Further a painting device could be coupled with the drone 2506 as well. The paint sprayed onto the surface of an object would join that object with the paint, the paint being first in liquid form and then in solid form when dried. Further still, the gripping mechanism 2502 could be replaced with other type of handling mechanisms, or alternatively, the welding device could be coupled to the drone 2506 directly, or through a tether.

Figure 25B:
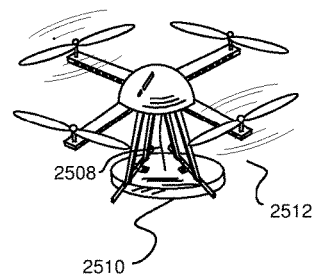
FIG. 25B depicts a drone coupled with an electromagnet.

FIG. 25B depicts a drone coupled with an electromagnet. An electromagnet is a type of magnet in which the magnetic field is produced by an electric current. The magnetic field disappears when the current is turned off. Electromagnets usually consist of a large number of closely spaced turns of wire that create the magnetic field. The wire turns are often wound around a magnetic core made from a ferromagnetic or ferrimagnetic material such as iron; the magnetic core concentrates the magnetic flux and makes a more powerful magnet. A drone 2512 is coupled to an electromagnet 2510. An conductive wire 2508 connects the drone 2512 and the electromagnet 2510 to supply the necessary electrical current for the magnetic field to be generated. The electromagnet 2510 is capable of pick up ferrous metals like iron and steel. The fact that the drone is able to fly to places sometimes hard to reach otherwise makes this embodiment very useful in pickup metals. Further it could be used in conjunction with other embodiments of the invention to work in manufacturing, repair and maintenance.

Figure 25C:
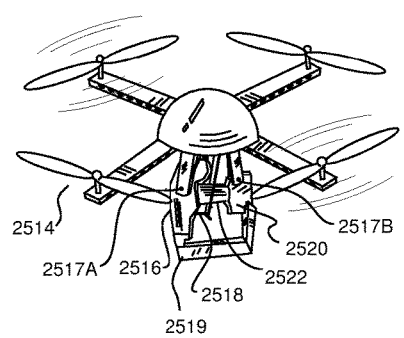
FIG. 25C depicts a drone coupled with a nail gun.

FIG. 25C depicts a drone coupled with a nail gun. A nail gun, nailgun or nailer is a type of tool used to drive nails into wood or some other kind of material. It is usually driven by electromagnetism, compressed air (pneumatic), highly flammable gases such as butane or propane, or, for powder-actuated tools, a small explosive charge. Nail guns have in many ways replaced hammers as tools of choice among builders. A drone 2514 is coupled with a nailgun 2516 through fasteners 1017A and 1017B. The handle of the nail gun is shown in 2522 and the trigger is shown in 2518. The nails come out of 1019. The battery housing is shown in 2520. The nail gun could be an existing nail gun with some adaptation for being used with a drone, or alternatively, the main components could be integrated with a drone. This embodiment could be used to install roofs, which typically requires workers to be working on the roof. Working on a roof is sometimes dangerous and inefficient. With this embodiment, putting nails on roof could be easier. The drone could move anywhere on the roof and reduce the danger posed to the workers if they have to be present on the roof. This embodiment shows an object joining mechanism joining a first object, which is the roof, and a second object, which is the shingles.

Figure 25D:
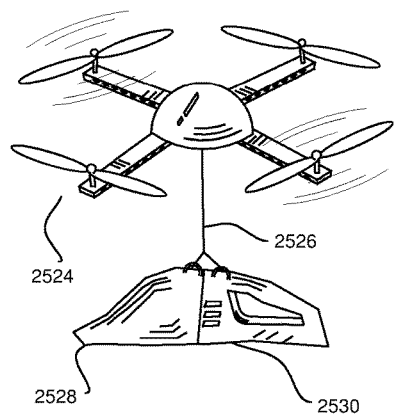
FIG. 25D depicts a drone coupled with a vacuum.

FIG. 25D depicts a drone coupled with a vacuum. A drone 2524 is coupled with a vacuum 2530 through a tether 2526. The nozzle 2528 of the vacuum 2530 picks up objects from a surface, i.e., removes an object from its original place. This embodiment could be useful for janitorial or manufacturing purpose. The tether 2526 could be replaced with other means of coupling, such as a rod. The vacuum 2530 could be a readily available commercial portable vacuum cleaner or could be integrated with the drone, eliminating some housing or common components between the drone and the vacuum. The vacuum sucks air from around an object so that object gains air lifting which makes it easy to be sucked into the vacuum cleaner. Further it is easy to see that the vacuum cleaner could be replaced with a blower, which blows air out or a nozzle instead of sucking air from a nozzle in the vacuum case. The blower blows air around an object and the object is prone to be removed from its original place.

Further the different tools could form any combination to carry out two or more functions. For instance, a drill and a vacuum combined could drill a hole in wood and at the same time the drill dust could be vacuumed away by the vacuum cleaner. The drill and vacuum combination could be installed on a drone. Similar combinations are innumerable with many types of tools specifically disclosed here and tools a person in the art would easily come up with based on the specification.

Further, the control of the tools could be done remotely by a person or software through communication modules carried by a drone. And a drone is typically equipped with camera, microphone and other types of sensors, which send images, sounds and other information back remotely to the controlling person or software. For instance, the nail gun embodiment sends images of the roof and the shingles to a controlling center remotely. A human or a software application analyzes the job site and determine the force, speed and place when a nail is being put on the roof. The instructions are remotely sent back to the nailgun to carry out. The process could be further automated by programming the computer onboard the drone of the embodiment so that the drone could carry out the actions autonomously, without relying on remote instructions.

Figure 26:
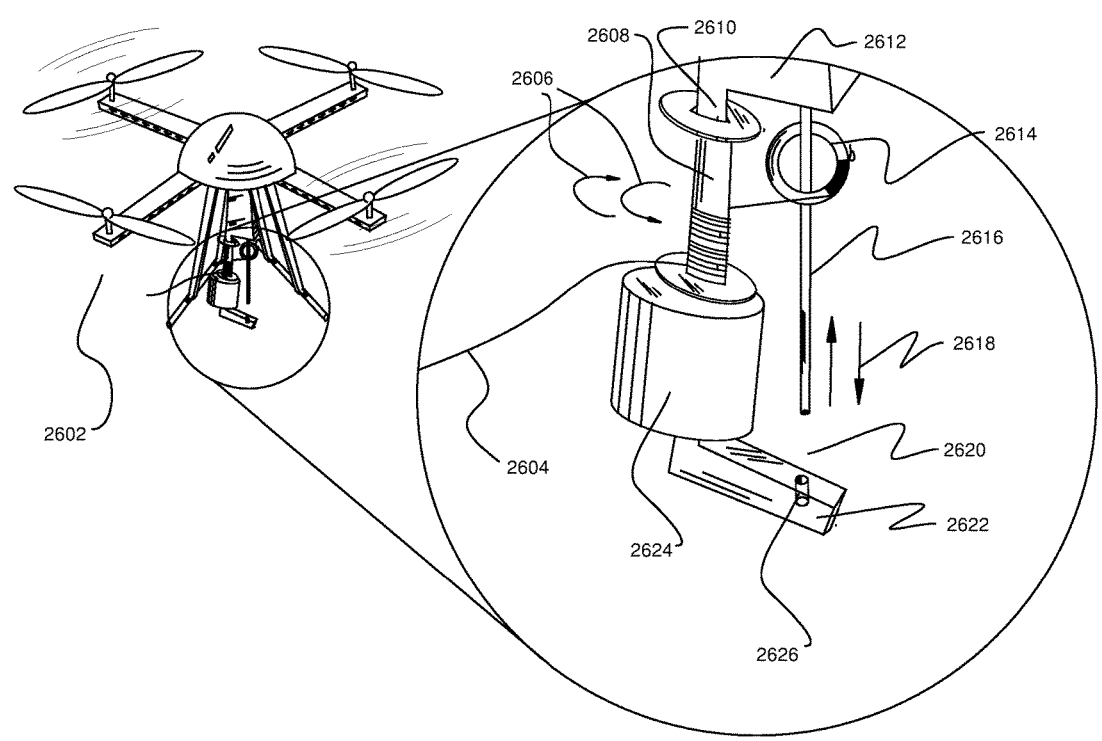
FIG. 26 depicts a drone, a tether reeling mechanism, and a tether releasing mechanism combined.

FIG. 26 depicts a drone, a tether extension and retraction mechanism, and a tether releasing mechanism combined. A drone 2602 has an actuator housing 2612 attached to its body. The actuator's thrust rod 2616 moves in two directions up and down as shown in 2618. When the thrust rod 2616 moves downward and engages a hole 2626 in the lower fixed arm 2622, an enclosure is formed by the thrust rod 2616, the lower fixed arm 2622, the fixed upper arm 2610, and the actuator housing 2612, therefore a tether terminator 2614 is locked inside the enclosure. Then the thrust rod 2616 moves upward, and opening 2620 is created which would allow the tether terminator 2614 to disengage from the opening 2620 and separate from the drone. A motor 2624 is fitted on the upper arm 2610, and a reel 2608 is coupled to the motor 2624. The reel can revolve freely around the upper arm 2608 in the directions depicted in 2606 as a resulting of the motor 2624's work. A tether 2604 is connected to the tether terminator 2614.

The reel 2608's revolving action causes the tether 2604 to extend and retract. In the case the tether is fully disengaged from the reel, the auto releasing mechanism described earlier enables the tether to separate from the drone completely. Both the extending and retracting mechanism, and the auto releasing mechanism are controlled by the drone 2602 or remotely.

Figure 27A:
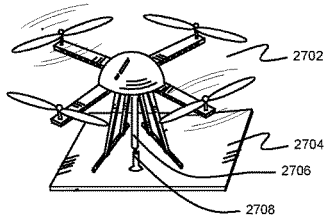
FIG. 27A depicts a UAV with anti crash airbag before the airbag is deployed.

FIG. 27A depicts a UAV with anti crash airbag before the airbag is deployed. The UAV 2702 has at least one airbag 2704 fitted to its body. A compressed air canister 2706 is fastened to the body of the UAV 2702. The opening of the canister 2706 is directly leading to the airbag air intake 2708. In some embodiments, the compressed air canister 2706 could be replaced by other means for inflating an airbag, such as explosives.

Figure 27B:
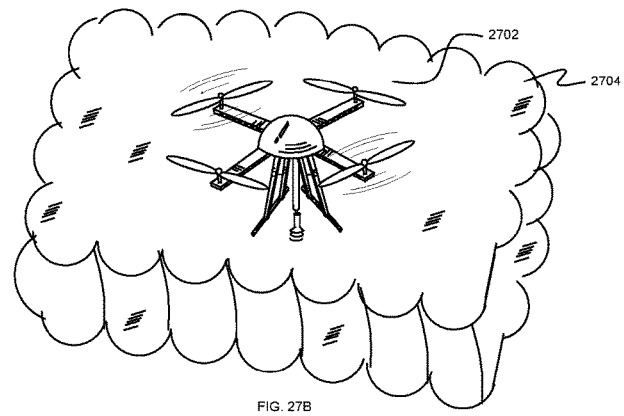
FIG. 27B depicts a UAV with anti crash airbag after the airbag is deployed.

FIG. 27B depicts a UAV with anti crash airbag after the airbag is deployed. The airbag 2704 is being deployed. The air cushion affords the UAV 2702 to cause less damage after it loses control and crashes into ground. Please note there is one airbag depicted in the figure, however many airbags of a variety of shapes could be used for protecting different parts of the UAV's impact.

Figure 27C:
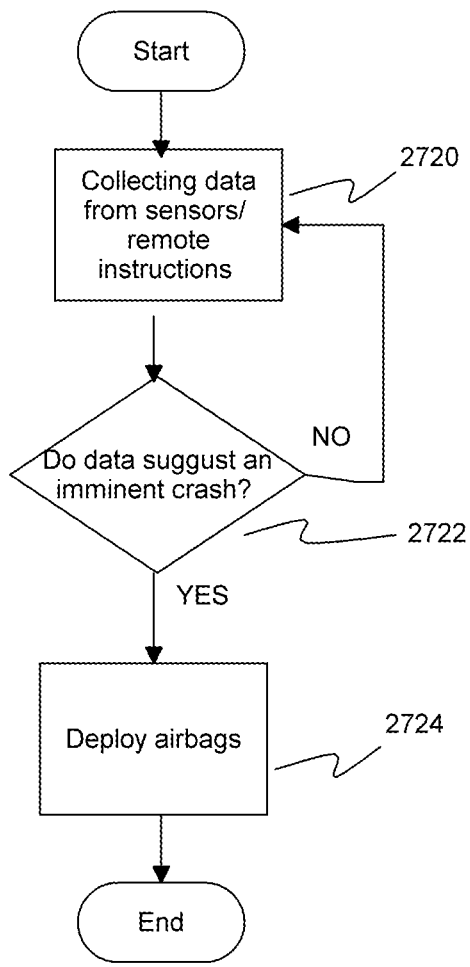
FIG. 27C depicts the flowchart on how a UAV with anti crash airbag is deployed.

FIG. 27C depicts the flowchart on how a UAV with anti crash airbag is deployed. Step 2720 collects the data from sensors input or from the remote instructions. The sensors could include a plurality of accelerometers to detect downward unwanted movement, altitude meter to detect the change of altitude and other sensors. These sensors individually or collectively could determine whether or not the UAV is in imminent danger of crashing. Human input or computer input could also activate the deployment of the airbags.

Step 2722 determines if data suggest an imminent crash. If the answer is yes, then the airbag is deployed in step 2724. The actual deployment of the airbag should take less than one second.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A system, comprising:
   an unmanned aerial vehicle (UAV);
   a first tether wherein its first end is connected to the UAV; and
   a second tether wherein its first end is connected to the second end of the first tether;
   wherein the first tether has lower tensile strength than the second tether
   an object being connected to the tether;
   wherein the object is a tool.

2. The system of claim 1, wherein the first tether is being spooled, and the spool is being carried by the UAV.

3. The system of claim 1, further comprising a moving vehicle from which the UAV is being released.

4. The system of claim 1, wherein the UAV has a release mechanism to release the first tether.

5. The system of claim 1, further comprising an object being connected to the second tether.

6. A method for using an unmanned aerial vehicle (UAV), and a plurality of tethers comprising at least a first tether and a second tether wherein the first tether has less tensile strength than the second tether for transporting an object to a desired location, comprising:
   connecting the first end of the first tether to the UAV;
   connecting the second end of the first tether to the first end of the second tether;
   connecting the object to the second tether;
   controlling the UAV to fly to the desired destination; and
   reeling the first tether so that the object is being dragged to the desired location,
   wherein the object is a tool for assisting the reeling.

7. The method according to claim 6, further comprising releasing the UAV from a moving vehicle.

8. The method according to claim 6, further comprising releasing the first tether from the UAV.

9. An apparatus comprising:
   a first unmanned aerial vehicle (UAV); a second UAV; and
   a tether wherein its first end is being connecting the first UAV, and its second end is being connected to the second UAV; and
   an object being connected to the tether;
   wherein the object is a tool.

10. The apparatus according to claim 9, wherein the first UAV comprises a mechanism to release the first end of the tether.

11. The apparatus according to claim 9, further comprising:
    a spool being placed in the first UAV for reeling the tether.

* * * * *